(12) United States Patent
Bengtsson et al.

(10) Patent No.: US 9,200,313 B2
(45) Date of Patent: *Dec. 1, 2015

(54) LYSIS AND REVERSE TRANSCRIPTION FOR MRNA QUANTIFICATION

(75) Inventors: Martin Bengtsson, Limhamn (SE); Michael Kubista, Moelndal (SE); Anders Stahlberg, Moelndal (SE); Linda Stroembom, Goteborg (SE)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 284 days.

This patent is subject to a terminal disclaimer.

(21) Appl. No.: 12/797,878

(22) Filed: Jun. 10, 2010

(65) Prior Publication Data

US 2011/0136180 A1 Jun. 9, 2011

Related U.S. Application Data

(63) Continuation of application No. 12/582,737, filed on Oct. 21, 2009, now abandoned, which is a continuation of application No. PCT/EP2008/003452, filed on Apr. 29, 2008.

(30) Foreign Application Priority Data

May 3, 2007 (EP) ..................................... 07008961

(51) Int. Cl.
*C12Q 1/68* (2006.01)

(52) U.S. Cl.
CPC ..................................... *C12Q 1/6806* (2013.01)

(58) Field of Classification Search
None
See application file for complete search history.

(56) References Cited

U.S. PATENT DOCUMENTS

2002/0009794 A1 1/2002 Danenberg et al.
2008/0003575 A1* 1/2008 Michalik et al. .................. 435/6

FOREIGN PATENT DOCUMENTS

| EP | 1529841 A1 | 5/2005 |
|---|---|---|
| WO | 2005/090984 A1 | 9/2005 |
| WO | 2005/116245 A3 | 12/2005 |

OTHER PUBLICATIONS

Hartshorn et al. (BMC Biotechnol., 2005, 5:2, p. 1-13).*
Chin et al. (Lab on a Chip, 2007, vol. 7, p. 41-57).*
International Search Report issued Aug. 6, 2008 in PCT Application No. PCT/EP2008/003452.
International Preliminary Report on Patentability issued May 20, 2009 in PCT Application No. PCT/EP2008/003452.
Bengtsson, Martin et al., Gene expression profiling in single cells from the pancreatic islets of Langerhans reveals lognormal distribution of mRNA levels, Genome Research, 2005, pp. 1388-1392, vol. 15.
Blake, William J. et al., Noise in eukaryotic gene expression, Nature, Apr. 10, 2003, pp. 633-637, vol. 422.
Boom, R. et al., Rapid and Simple Method for Purification of Nucleic Acids, Journal of Clinical Microbiology, Mar. 1990, pp. 495-503, vol. 28, No. 3.
Bustin, S. A., Absolute quantification of mRNA using real-time reverse transcription polymerase chain reaction assays, Journal of Molecular Endocrinology, 2000, pp. 169-193, vol. 25.
Cai, Long et al., Stochastic protein expression in individual cells at the single molecule level, Mar. 16, 2006, pp. 358-362, vol. 440.
Chomczynski, Piotr and Sacchi, Nicoletta, Single-Step Method of RNA Isolation by Acid Guanidinium Thiocyanate-Phenol-Chloroform Extraction, Analytical Biochemistry, 1987, pp. 156-159, vol. 162.
Elowitz, Michael B. et al., Stochastic Gene Expression in a Single Cell, Science, Aug. 16, 2002, pp. 1183-1186, vol. 297.
Freeman, Willard M. et al., Quantitative RT-PCR: Pitfalls and Potential, BioTechniques, Jan. 1999, pp. 112-125, vol. 26.
Ginsberg, Stephen D., RNA amplification strategies for small sample populations, Methods, 2005, pp. 229-237, vol. 37.
Kawasaki, Ernest S., Microarrays and the Gene Expression Profile of a Single Cell, Annals of the New York Academy of Sciences, 2004, pp. 92-100, vol. 1020.
Levsky, Jeffrey M. et al., Single-Cell Gene Expression Profiling, Science, Aug. 2, 2002, pp. 836-840, vol. 297.
Liss, Birgit, Improved quantitative real-time RT-PCR for expression profiling of individual cells, Nucleic Acids Research, 2002, 9 pages, vol. 30, No. 17, e89.
Nolan, Tania et al., Quantification of mRNA using real-time RT-PCR, Nature Protocols, 2006, pp. 1559-1582, vol. 1, No. 3.
Olofsson, Charlotta S. et al., Fast insulin secretion reflects exocytosis of docked granules in mouse pancreatic B-cells, Pfugers Arch—European Journal of Physiology, 2002, pp. 43-51, vol. 444.
Peixoto, Antonio et al., Quantification of Multiple Gene Expression in Individual Cells, Genome Research, 2004, pp. 1938-1947, vol. 14.

(Continued)

*Primary Examiner* — Stephanie K Mummert
(74) *Attorney, Agent, or Firm* — Olga Kay

(57) ABSTRACT

The present invention is directed to a method for performing an RT-PCR for amplifying a target RNA comprising the steps of a) lysis of a cellular sample which is supposed to contain the target RNA with a lysis buffer comprising between 0.2 M and 1 M Guanidine Thiocyanate, b) diluting the sample to an extent such that Guanidine Thiocyanate is present in a concentration of about 30 to 50 mM, c) reverse transcribing in the presence of a mixture of first strand cDNA synthesis primers, the mixture consisting of oligo dT primers and random primers, and d) subjecting the sample to multiple cycles of a thermocycling protocol and monitoring amplification of the first strand cDNA in real time, characterized in that steps a) to c) are done in the same vessel.

19 Claims, 18 Drawing Sheets

(56) References Cited

OTHER PUBLICATIONS

Raj, Arjun et al., Stochastic mRNA Synthesis in Mammalian Cells, PLOS Biology, Oct. 2006, pp. 1707-1719, vol. 4, Issue 10, e309.

Ross, Ian L. et al., Transcription of individual genes in eukaryotic cells occurs randomly and infrequently, Immunology and Cell Biology, 1994, pp. 177-185, vol. 72.

Schuit, F. C. et al., Glucose stimulates proinsulin biosynthesis by a dose-dependent recruitment of pancreatic beta cells, Proceedings of the National Academy of Science USA, Jun. 1988, pp. 3865-3869, vol. 85.

Stahlberg, Anders et al., Properties of the Reverse Transcription Reaction in mRNA Quantification, Clinical Chemistry, 2004, pp. 509-515, vol. 50, No. 3.

Stahlberg, Anders et al., Comparison of Reverse Transcriptases in Gene Expression Analysis, Clinical Chemistry, 2004, pp. 1678-1680, vol. 50, No. 9.

Tang, Fuchou et al., MicroRNA expression profiling of single whole embryonic stem cells, Nucleic Acids Research, 2006, 7 pages, vol. 34, No. 2, e9.

Vandesompele, Jo et al., Accurate normalization of real-time quantitative RT-PCR data by geometric averaging of multiple internal control genes, Genome Biology, 2002, 12 pages, vol. 3, No. 7.

Weintraub, Harold, Formation of stable transcription complexes as assayed by analysis of individual templates, Proceedings of the National Academy of Science USA, 1988, pp. 5819-5823, vol. 85.

Yamada, Osamu et al., a new method for extracting DNA or RNA for polymerase chain reaction, Journal of Virological Methods, 1990, pp. 203-210, vol. 27.

Yamaguchi, Masahiko et al., Effect of Different Laboratory Techniques for Guanidinium-Phenol-Chloroform RNA Extraction on A260/A280 and on Accuracy of mRNA Quantitation by Reverse Transcriptase-PCR, PCR Methods and Application, May 1992, pp. 286-290, vol. 1, No. 4.

\* cited by examiner

LYSIS AND REVERSE TRANSCRIPTION FOR MRNA QUANTIFICATION

RELATED APPLICATIONS

This application is a continuation of U.S. application Ser. No. 12/582,737 filed Oct. 21, 2009, now abandoned which is a continuation of PCT/EP2008/003452 filed Apr. 29, 2008 and claims priority to EP07008961.0 filed May 3, 2007.

FIELD OF THE INVENTION

The present invention provides a method for mRNA measurements. Using quantitative PCR, together with optimized procedures for cell collection, lysis and reverse transcription, the method allows the study of transcript numbers, distributions, correlations, and gene induction even at the single cell level.

BACKGROUND

Cells in a population are in many aspects unique in their characteristics, even in a seemingly homogenous culture or tissue. Gene expression levels show large cell-cell variations, due to external (extrinsic) and internal (intrinsic) sources of factors. Likewise, when exposed to identical stimuli, cells often behave stochastically. This means that data obtained from a population of cells can not be assumed to reflect the behavior of the individual cell. It has been suggested that cells can respond to stimuli by bursts in transcriptional activity and operate as a binary switch; that is in an all-or-none fashion.

To determine whether two transcripts are expressed in a parallel (expression high at the same time) or anti-parallel (one is high when the other is low), transcription analysis at the level of the individual cell is required. When groups of cells are analyzed at the same time, important information is lost. For example, it is not possible to discriminate between a small change in gene transcription occurring in every cell as opposed to major changes in only a few cells. Furthermore, cell heterogeneity in tissues makes cell-type specific analysis difficult. These issues are resolved by measurements in individual cells.

A typical eukaryotic cell contains about 25 pg of RNA of which less than 2% is mRNA. This corresponds to a few hundred thousands of transcripts of the 10,000 genes that are expressed in each cell at any particular point in time. Imaging techniques such as multiplex fluorescent in situ-hybridization (FISH) can monitor gene transcriptional activity spatially within a single cell by labeling of specific mRNAs and may be applied to living cells to provide temporally resolved glimpses of the complexity of the transcription machinery. Protein levels in single cells have been measured quantitatively in bacteria and yeast using fluorescent reporter proteins. For a complete transcriptome analysis of a single cell, microarrays, preceded by non-specific amplification of cDNA, are used. The most widespread method for single cell mRNA analysis is reverse transcription polymerase chain reaction (RT-PCR), and the related quantitative real-time RT-PCR (qRT-PCR). This technique offers superior sensitivity, accuracy, and dynamic range compared to alternative methods for mRNA measurements. The number of transcripts that can be readily analyzed in the single cell is small, but pre-amplification of cDNA vastly increases this number.

However, the protocols for single cell analysis that exist in the art so far are useful only with respect to the detection of abundantly expressed targets. These methods do not provide the sensitivity required to detect target mRNAs that are expressed as a comparatively low level.

SUMMARY OF THE INVENTION

Thus, in a first aspect, the present invention is directed to a method for performing an RT-PCR for amplifying a target RNA comprising the steps of
  a) in a sample vessel, lysis of a biological sample consisting of only a few cells which is supposed to contain said target RNA with a lysis buffer comprising between 0.05 M and 1 M Chaotropic agent
  b) in the same sample vessel, diluting said sample to an extend such that Chaotropic agent is present during step c) in a concentration of about 10 to 60 mM
  c) in the same sample vessel without any intermediate purification step reverse transcribing said target RNA in the presence of a mixture of first strand cDNA synthesis primers into a first strand cDNA, said mixture consisting of primers hybridizing to a poly-A sequence and/or random primers
  d) amplifying said first strand cDNA by means of subjecting said sample to multiple cycles of a thermocycling protocol.

Preferably, amplification of said first strand cDNA during said thermocycling protocol is monitored in real time.

This method is typically applicable if the sample comprises only a limited number of cells, i.e. not more that 1000 cells, and preferably less than 100 cells. In particular, the method is applicable even if the sample comprises only less than 10 cells or a single cell.

Preferably, said chaotropic agent is Guanidine Thiocyanate. Alternatively said chaotropic agent may be come selected from a group consisting of Guanine Hydrochloride, Potassium Cyanate and Ammonium Sulphate.

Preferably, the lysis buffer comprises between about 0.2 and 0.5 M Chaotropic agent.

Also preferably, during step c), i.e. during the reverse transcriptase reaction, Chaotropic agent is present in a concentration of about 10-60 mM, more preferably between 30 and 50 mM and most preferably about 40 mM.

Also preferably, step a) comprises the addition of a carbohydrate, which is preferably a sugar or a dextran in order to avoid evaporation of low sample volumes.

Optionally, the reverse transcriptase reaction may be performed in the presence of 0.5 to 2% of a non ionic detergent, which is preferably NP 40 (octyl phenoxylpolyethoxyethanol). In one embodiment, such non ionic detergent may already be added to the sample during step a).

In one embodiment, step a) is performed for at least 5 minutes at ambient temperature or even below.

In another embodiment, the incubation of step a) may be performed between 55-85° C. in the presence of Proteinase K. Then, between step a) and step b) or step b) and step c), the sample may be incubated for at least 5 minutes at a temperature between about 80° C. to 90° C. in order to destroy any residual Proteinase K activity Also according to the present invention, step a) may be performed in the presence of a double strand specific DNAse, preferably DNAse I or Shrimp Nuclease. In case of using DNAse I, it is advantageous, if between step a) and step b) or step b) and step c), the sample is incubated for at least 5 minutes at a temperature between about 80° C. to 90° C.

Optionally, the sample is frozen at temperatures between about −20° C. and −80° C. immediately prior to step b). That means that after freezing, no additive as disclosed above is being added anymore prior to step b).

According to the present invention it is highly preferable if said mixture of cDNA synthesis primers comprises both: primers hybridizing to a poly-A sequence as well as random primers.

The random primer is usually a random hexamer primer. The primers hybridizing to a poly-A sequence are usually oligo-dT primers or Oligo-dU primers. In a preferred embodiment, said primers hybridizing to a poly-A sequence and random primers are present in equal amounts. In another preferred embodiment, which is compatible with the above mentioned one, said primers hybridizing to a poly-A sequence and random primers are present in concentrations between 1 µM and 5 µM each. Highly preferred are concentrations of about 2.5 µM each.

In a very specific embodiment suitable for analysis of multicellular biological samples, the method according the present invention comprises the steps of
  a) lysis of a biological sample which is supposed to contain said target RNA with a lysis buffer comprising between 0.2 M and 1 M Guanidine Thiocyanate by means of
     incubation for at least 5 minutes at a temperature at ambient temperature between 16° C. and 24° C. in the absence of proteinase K or between 55-85° C. in the presence of Proteinase K
     incubation for about 2 to 10 minutes at 95° C.
     freezing said sample at −25° C.
  b) diluting said sample to an extent such that Guanidine Thiocyanate is present in a concentration of about 20 to 60 mM.
  c) reverse transcribing in the presence of a mixture of first strand cDNA synthesis primers, said mixture consisting of random sequence primers and primers hybridizing to a poly-A sequence.
  d) subjecting said sample to multiple cycles of a thermocycling protocol and monitoring amplification of said first strand cDNA in real time.

In another very specific embodiment suitable for analysis of single cells, the method according the present invention comprises the steps of
  a) lysis of a single cell which is supposed to contain said target RNA with a lysis buffer comprising between 0.2 M and 1 M Guanidine Thiocyanate by means of
     incubation for at least 10 minutes at a temperature between at ambient temperature between 16° C. and 24° C. in the absence of proteinase K or between 55-85° C. in the presence of Proteinase K
     freezing said sample at −75° C. to −80° C.
  b) diluting said sample to an extend such that Guanidine Thiocyanate is present in a concentration of about 30 to 50 mM.
  c) reverse transcribing in the presence of a mixture of first strand cDNA synthesis primers, said mixture consisting of primers hybridizing to a poly-A sequence and random primers
  d) subjecting said sample to multiple cycles of a thermocycling protocol and monitoring amplification of said first strand cDNA in real time.

NP-40 and four with 0.5 M GTC according to the disclosed invention. Intra-assay variation for each sample is shown.

Figure 10A:
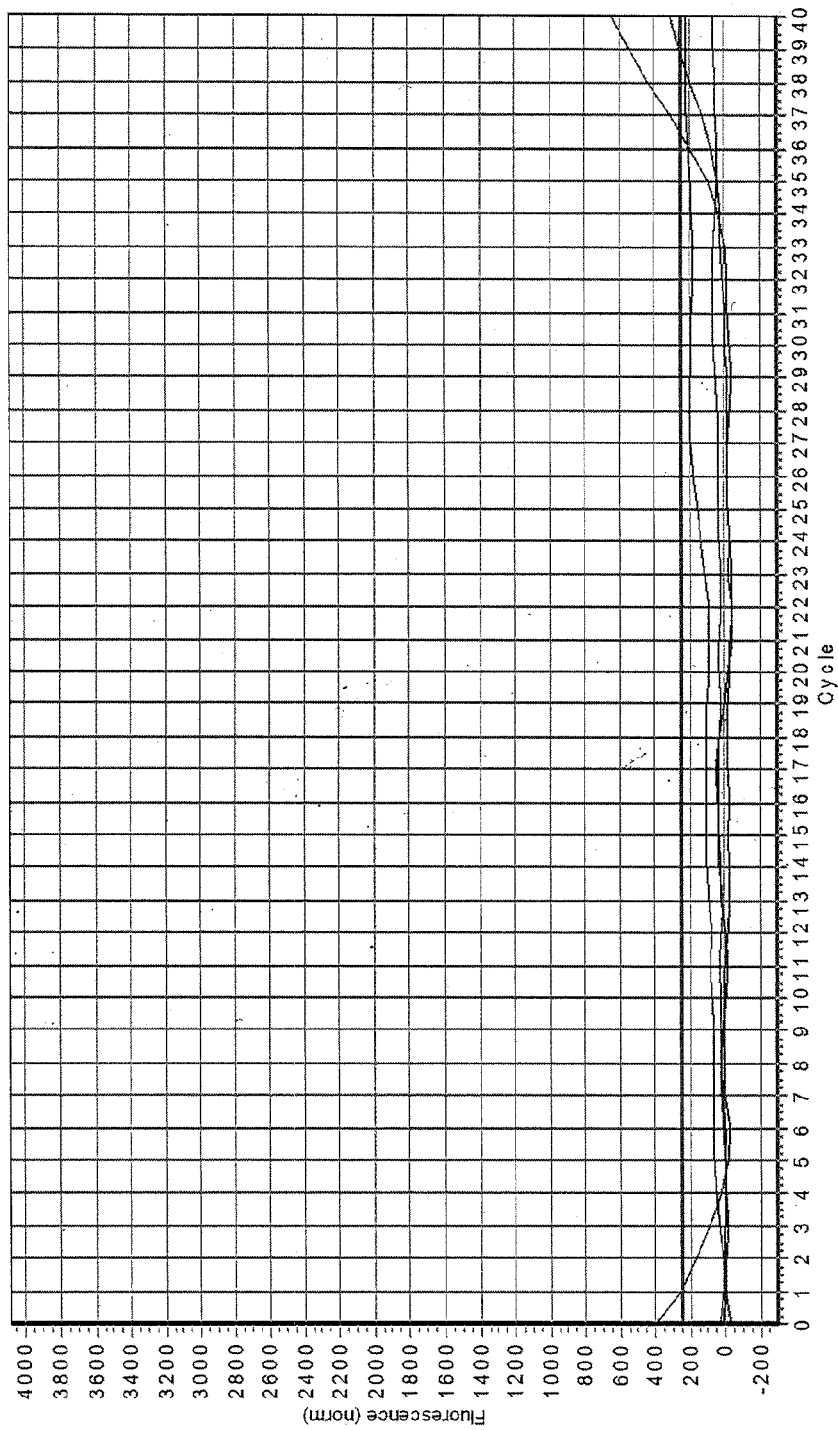
Figure 10B:
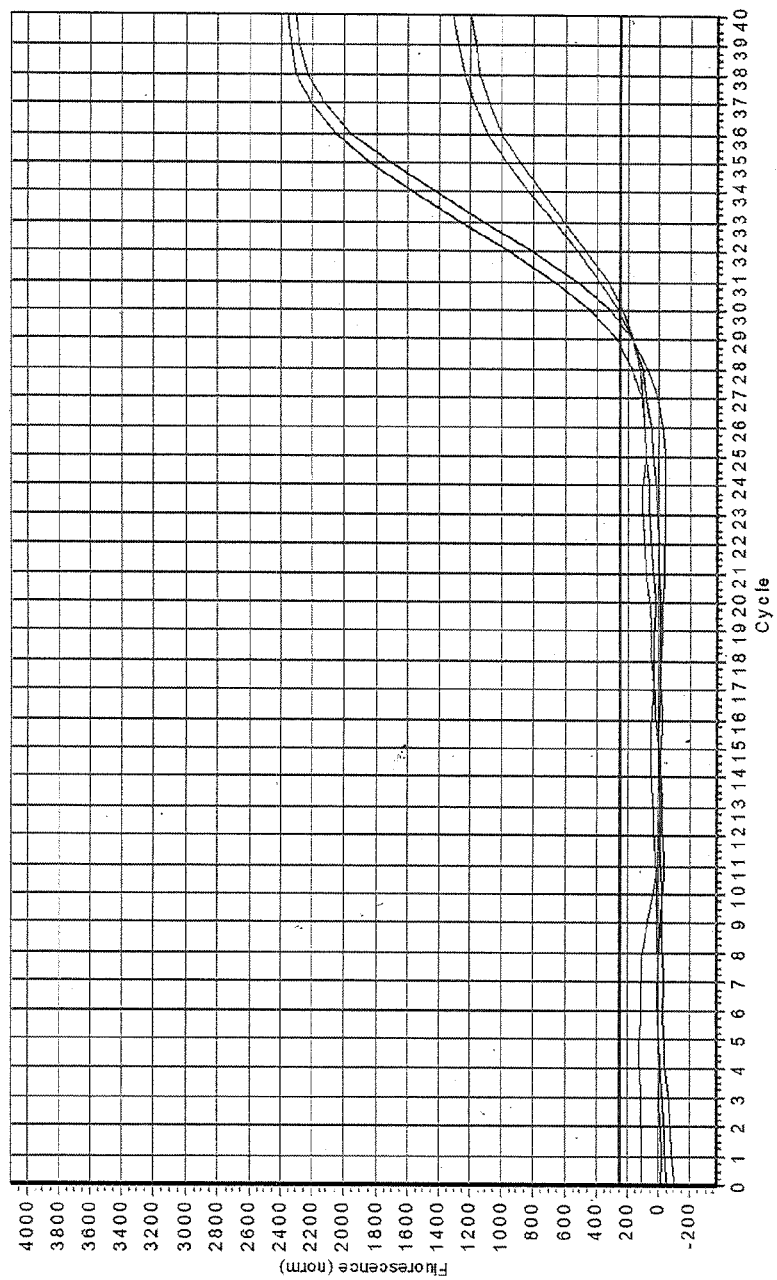

FIG. 10: FIG. 10A: Aliquot extracted with the RNeasy Micro kit from Qiagen. Mean Ct for HPV16E7 was 37.7. HPV 16E6 was not possible to detect. FIG. 10B: Aliquot extracted using the disclosed invention. Mean Ct for HPV16E6 was 30.6 and mean CT for HPV16E7 was 29.2.

Figure 11:
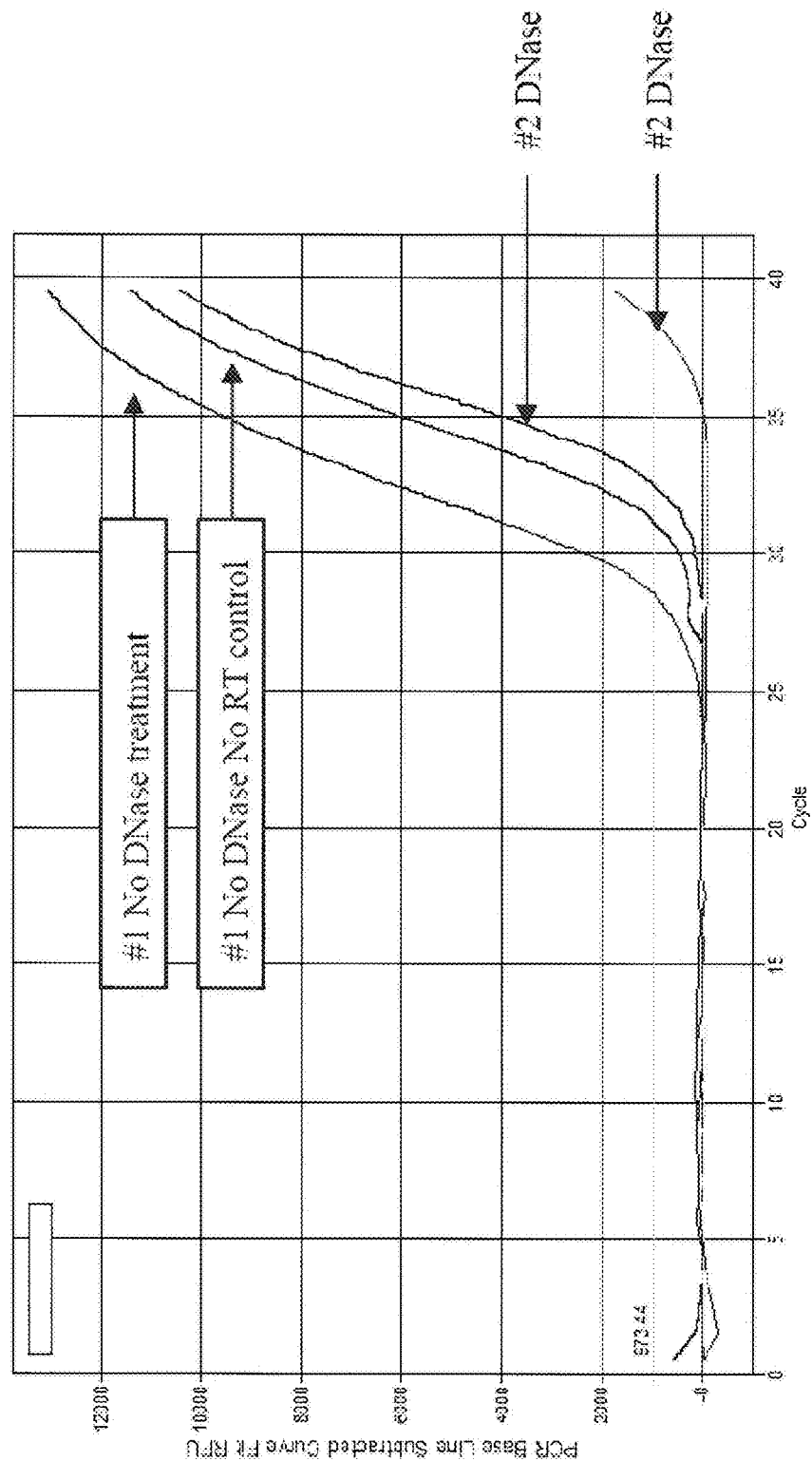
Figure 11A:
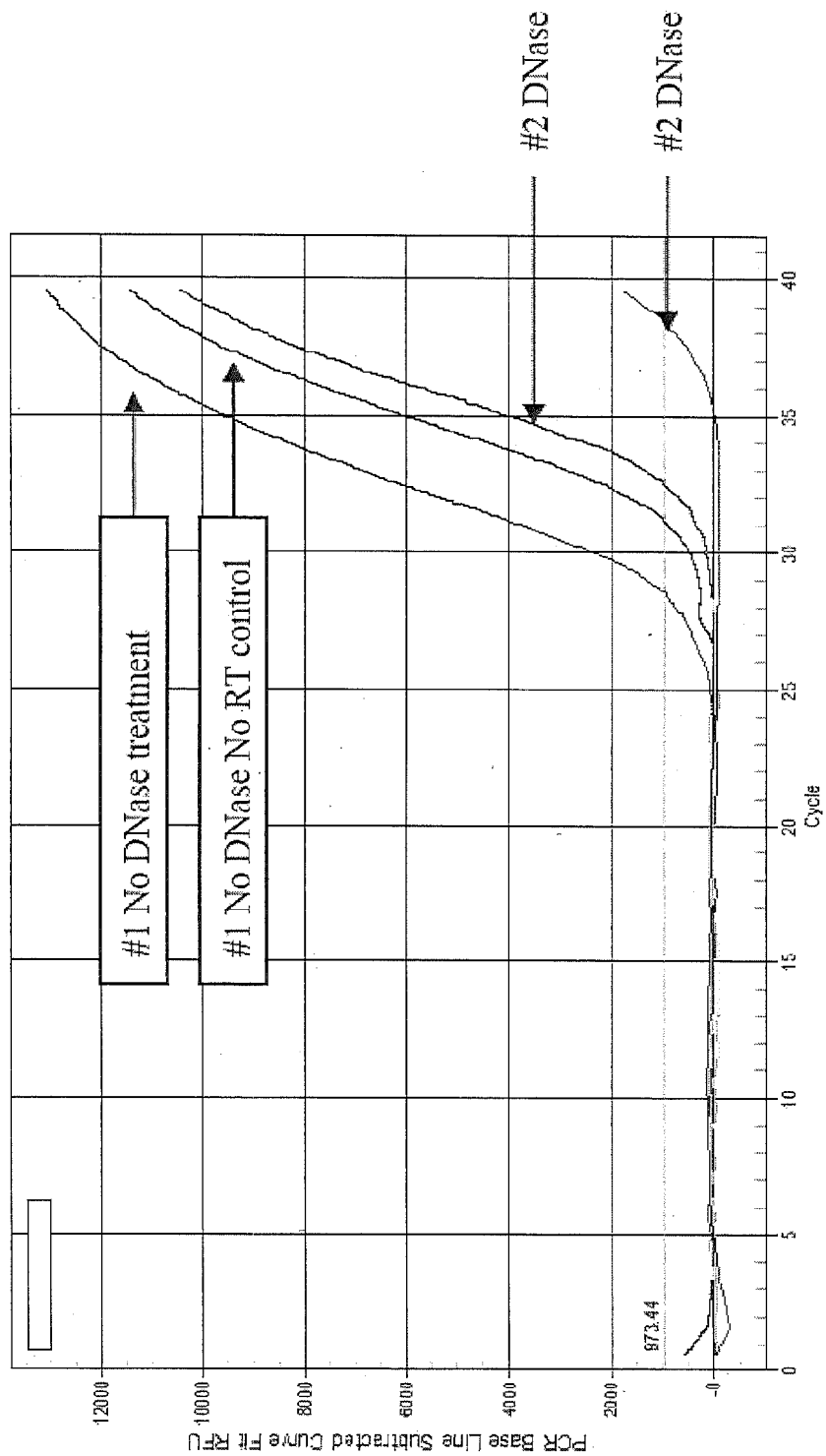
Figure 11B:
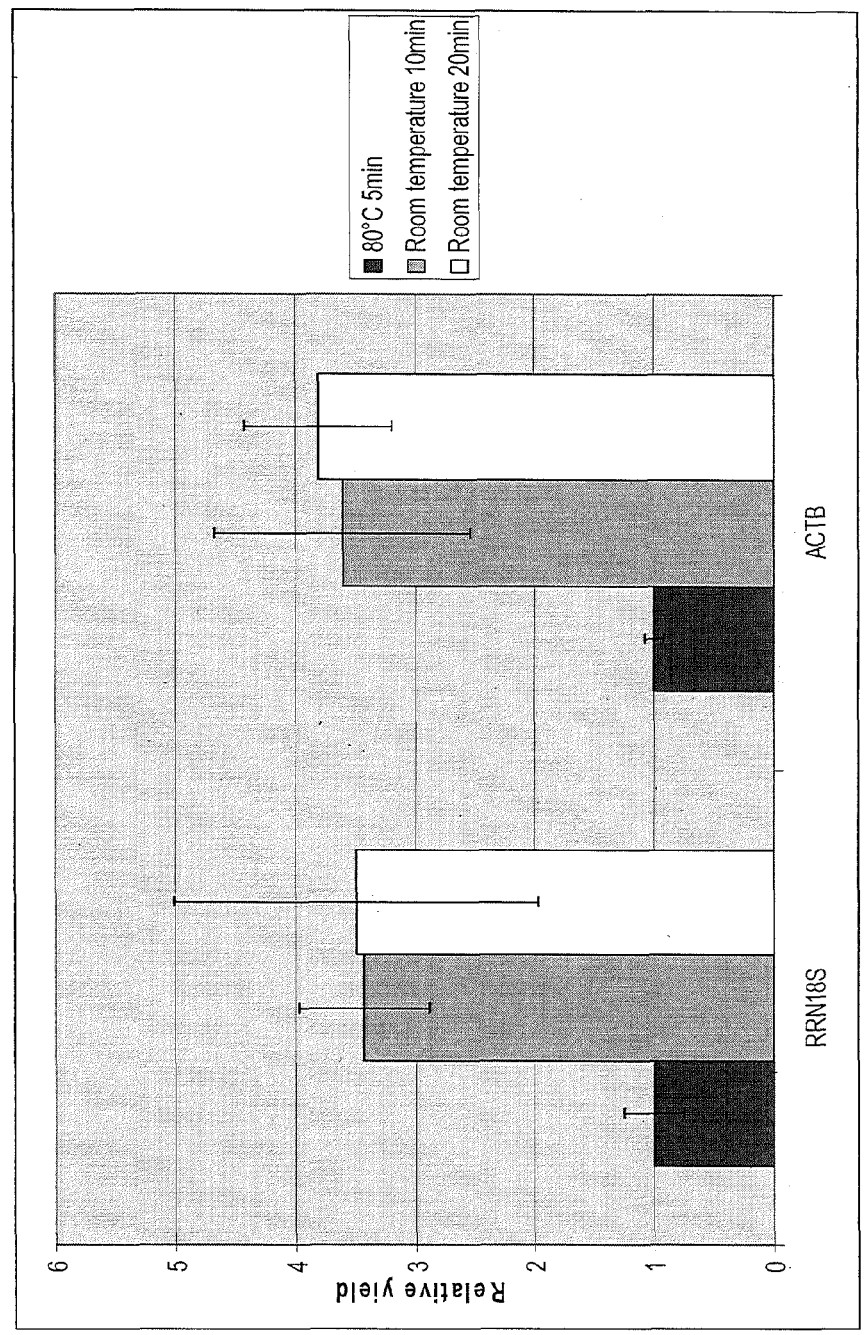

FIG. 11: Extraction and analysis of Caski cells. QPCR analysis of HPV16E6 (FIG. 11A) and 18S cDNA (FIG. 11B) +/−DNase treatment +/−RT.

Figure 12:
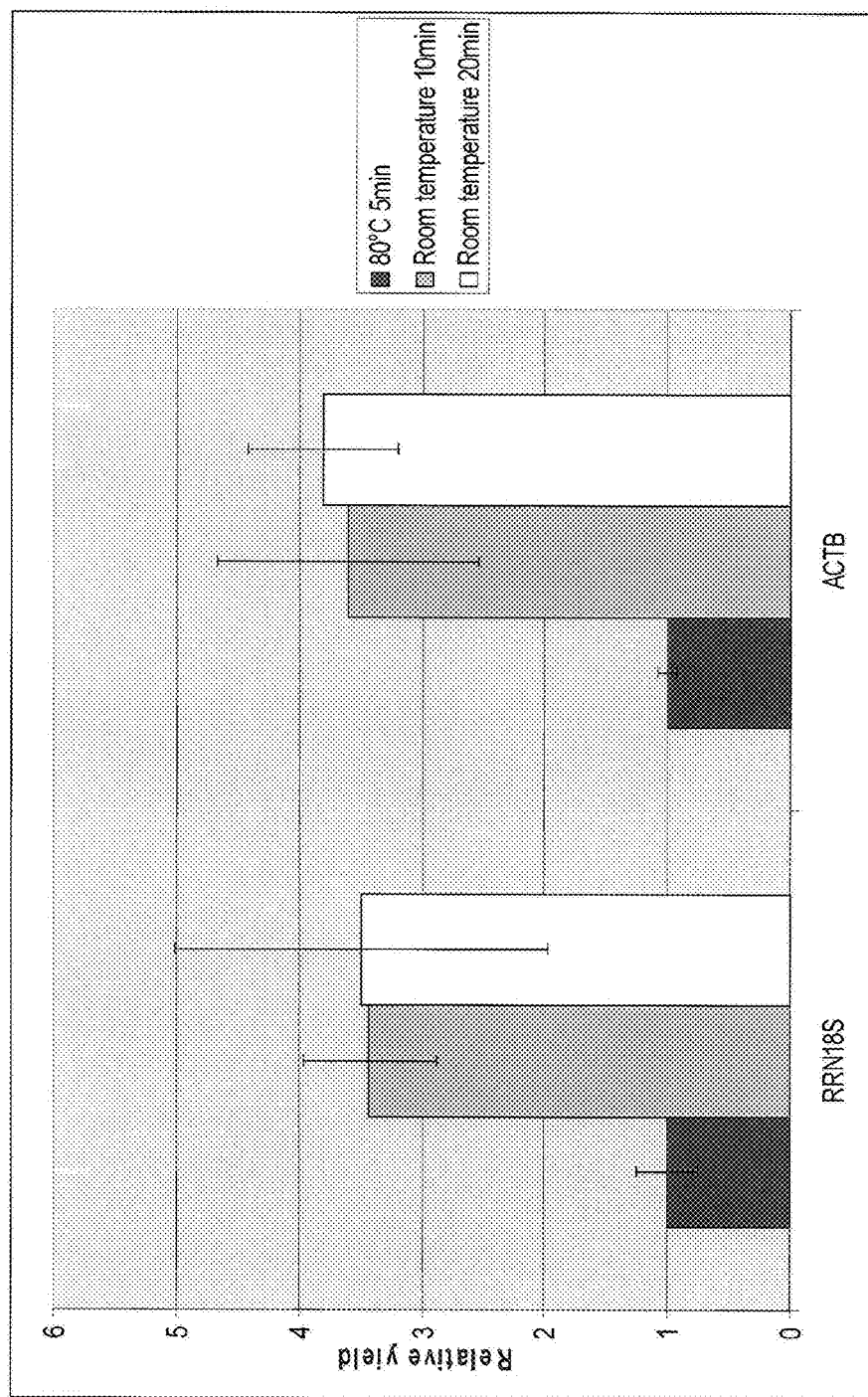

FIG. 12: Genes' expressions in pelleted THP1 monocytes prepared using the disclosed invention at different lysis temperatures, and measured with reverse transcription and qPCR. Y-axis shows the relative yield of cDNA per sample.

DETAILED DESCRIPTION OF THE INVENTION

According to the present invention, it is possible to perform a lysis of eukaryotic cells or even prokaryotic cells in a certain reaction vessel and in the same reaction vessel performing a Reverse Transcriptase reaction in order to generate single stranded cDNA. Thus, the present invention more precisely is directed to a method for performing an RT-PCR for amplifying a target RNA comprising the steps of
a) lysis of a biological sample which is supposed to contain said target RNA in a sample vessel with a lysis buffer comprising between 0.05 M and 1 M of a chaotropic agent
b) diluting said sample to an extend such that said chaotropic agent is present during step c) in a concentration of about 10 to 60 mM in said sample vessel
c) without any intermediate purification step reverse transcribing said target RNA in the presence of a mixture of first strand cDNA synthesis primers, said mixture consisting of primers hybridizing to a poly-A sequence and/or random primers and/or target specific primers in said sample vessel
d) subjecting said sample to multiple cycles of a thermocycling protocol and preferably monitoring amplification of said first strand cDNA in real time.

In order to control the process of harvesting, cell lysis and reverse transcription, the samples may be spiked with a control RNA. The control RNA preferably is an artificial RNA which during the step of reverse transcription is transcribed into a cDNA that can be discriminated from the RNA of the sample. In case of using specific primers for the Reverse Transcription step, the artificial RNA may be derived from in vitro transcription of a genetically engineered DNA template that either comprises an insertion or only partially represents the target sequence which shall become analyzed.

The biological sample may contain either eukaryotic cells or prokaryotic cells which are in suspension. In case there are only a few eukaryotic cells such as a single cell, preferably less then 10 cells, more preferably less than 100 cells or at least less than 1000 cells, the suspension volume may also be very low. Preferably, the suspension volume is less then 20 µl and most preferably less than 5 µl.

Biological samples containing only a few cells may be generated for example by means of dilution of a cell suspension culture. For these cases, the lysis reagent according to the invention may be added directly to the cell suspension as long as the lysis reagent is provided at least in a 5:1 V/V excess, or preferably in a 10:1 V/V excess.

Biological samples consisting of a small number of cells such as not more than 100 cells, preferably not more than 10 cells and most preferably single cells only, may also be generated by means of fluorescence activated cell sorting (FACS). In this case, the sorted cells may be directed into a well such as a well within a microtiter plate, which already contains the lysis buffer according to the invention.

However, the method according to the present invention is also applicable for a larger number of cells that have been cultivated in suspension. Preferably, large cell numbers are first collected by appropriate means of centrifugation. Optionally said collection comprises a washing step in an appropriate buffer system such as a PBS buffer. Subsequently the lysis buffer is added. For lysis of the complete sample, the sample may be shaken vigorously, for example by means of vortexing.

In one embodiment, step a) of the present invention is performed in the presence of a non ionic detergent such as NP40. Alternatively, step a) comprises the addition of a carbohydrate, which is preferably a sugar or a dextran. Both components result in an effective avoidance of evaporation effects, if samples with only small volumes need to be processed. If NP40 or another non ionic detergent is added, then the amount of detergent should be chosen in such a way that during step c) said detergent is present in a V/V amount of 0.5 to 2%.

In a preferred embodiment, the lysis buffer according to the present invention additionally contains polyinosinic acid. Advantageously, 0.2-5 ng and most advantageously, 0.5-2 ng polyinosinic acid are contained in 1 µl of lysis buffer.

Cell harvesting and lysis according to the present invention may be performed at various different temperatures. In one embodiment, step a) of the inventive method is performed in the absence of Proteinase K for at least 5 minutes i.e. between 16° C. and 24° C. The maximum time which is required for lysis under these circumstances is about 30 minutes. Similarly, step a) of the inventive method in the absence of Proteinase K can be performed for at least 10 minutes even below ambient temperature, but above 5° C. The maximum time which is required for lysis under these circumstances is about 60 minutes. These conditions are very favorable for the avoidance of any evaporation effects, if samples with small volumes are processed. It also eliminates the need for heating.

In an alternative embodiment of the present invention, step a) is performed for at least 5 minutes at a temperature between about 55° C. to 85° C., preferably in the presence of Proteinase K in concentrations of about 0.05 to 5 mg/ml and preferably 0.1-1 mg/ml. Optionally, said Proteinase K may be irreversibly inactivated by means of subsequent incubation either between step a) and step b) or between step b) and step c) for at least 5 minutes but usually not more than 30 minutes at a temperature between about 80° C. to 90° C.

As according to the present invention, cell lysis and reverse transcription are performed in the same reaction vessel, it has been proven to be highly advantageous if the genomic DNA that is contained in the lysed cells can selectively be removed, while the cellular RNA is maintained intact. The most effective possibility to achieve this effect is an enzymatic removal by means of including a DNAse digestion step. Thus, in one major embodiment of the present invention, step a) is performed in the presence of a double strand specific DNAse. Preferably, such a DNAse is an exclusively double strand specific DNAs such as DNAse I or Shrimp DNAse (USB, Cat No: 78314).

However, if during step d) the single stranded cDNA is further be subjected to a DNA Polymerase catalyzed amplification reaction such as a PCR reaction, it is highly advantageous to inactivate said DNAse prior to the amplification reaction. Thus, for inactivation of DNAse activity, in a specific embodiment the sample is incubated for at least 5 minutes but not longer than 60 minutes between step a) and step b) or step b) and step c) at a temperature between about 80° C. to 90°. Alternatively, if the DNAse is Shrimp DNAse, the denaturation during the first cycle of the PCR reaction in step d) is usually sufficient.

All the different embodiments as outlined above have in common that cell lysis, dilution, any addition of additives and the Reverse Transcriptase reaction are carried out in the same reaction vessel. Therefore, the inventive method is particularly useful for high throughput analyses of multiple samples within an automated process. In this context, the multiple reaction vessels may be arranged together in the form of a microtiter plate as it is well known in the art. For example such a micro-titer plate may consist of 24, 96, 384, or 1536 separate reaction vessels arranged to standards that are established in the art. Then, the lysis reagent, the various additives and the reagents necessary for performing a Reverse Transcriptase reaction can be added to the samples by liquid handling roboting instruments.

Optimization of Conditions for Performing RT-PCR Analysis on Small Cell Numbers

Figure 1:
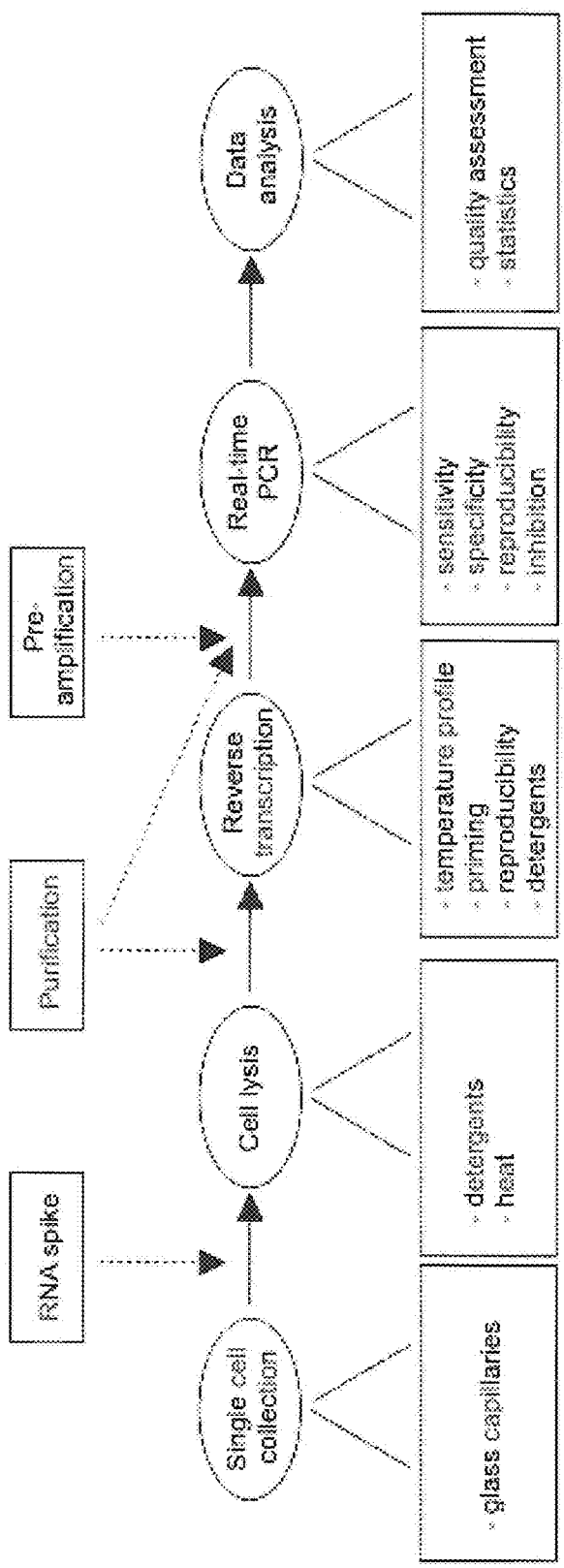
FIG. 1: Overview of single cell gene expression profiling using qRT-PCR. The alternatives and important issues for each step in the procedure that were addressed in this study are shown in boxes. Optional steps are shown in dotted arrows.

The method according to the present invention also permits gene expression profiling in only a few cells and even in a single cell. Species of mRNA in single cells or a few cells are quantified by qRT-PCR. At a cell population scale, gene expression levels are commonly normalized to reference genes [15]. The stochastic nature of single cells makes this approach invalid, leaving absolute quantification as the best option to compare transcript levels within and between cells. In order to improve the experimental protocols to optimize cell lysis and mRNA accessibility, the mRNA yield in the reverse transcription reaction and quality assessment were thus systematically analyzed. The method was demonstrated on single cells from the pancreatic islets of Langerhans in mouse, revealing transcript copy numbers, co-regulation of gene expression, and distribution of transcript expression levels. Dispersed cells were collected with a glass capillary, emptied in lysis buffer and analyzed with qRT-PCR. FIG. 1 outlines the experimental procedure. For quality assessment, an artificial RNA molecule based on the cyclophilin E (Ppie) gene was generated by in vitro transcription. An equal amount of Ppie RNA was added together with lysis buffer to all reaction tubes before the single cell was deposited into the tube. The RNA could reduce the adsorption of the cell itself or single cell mRNAs to surfaces. Samples with deviant cycle of threshold (Ct) values for the Ppie RNA spike may result from degradation by RNases. These samples were re-analyzed and, if the problem remained, excluded from further analysis. The presence of inhibitors may reduce the cDNA yield.

Optimization of Lysis and Buffer

Figure 2:
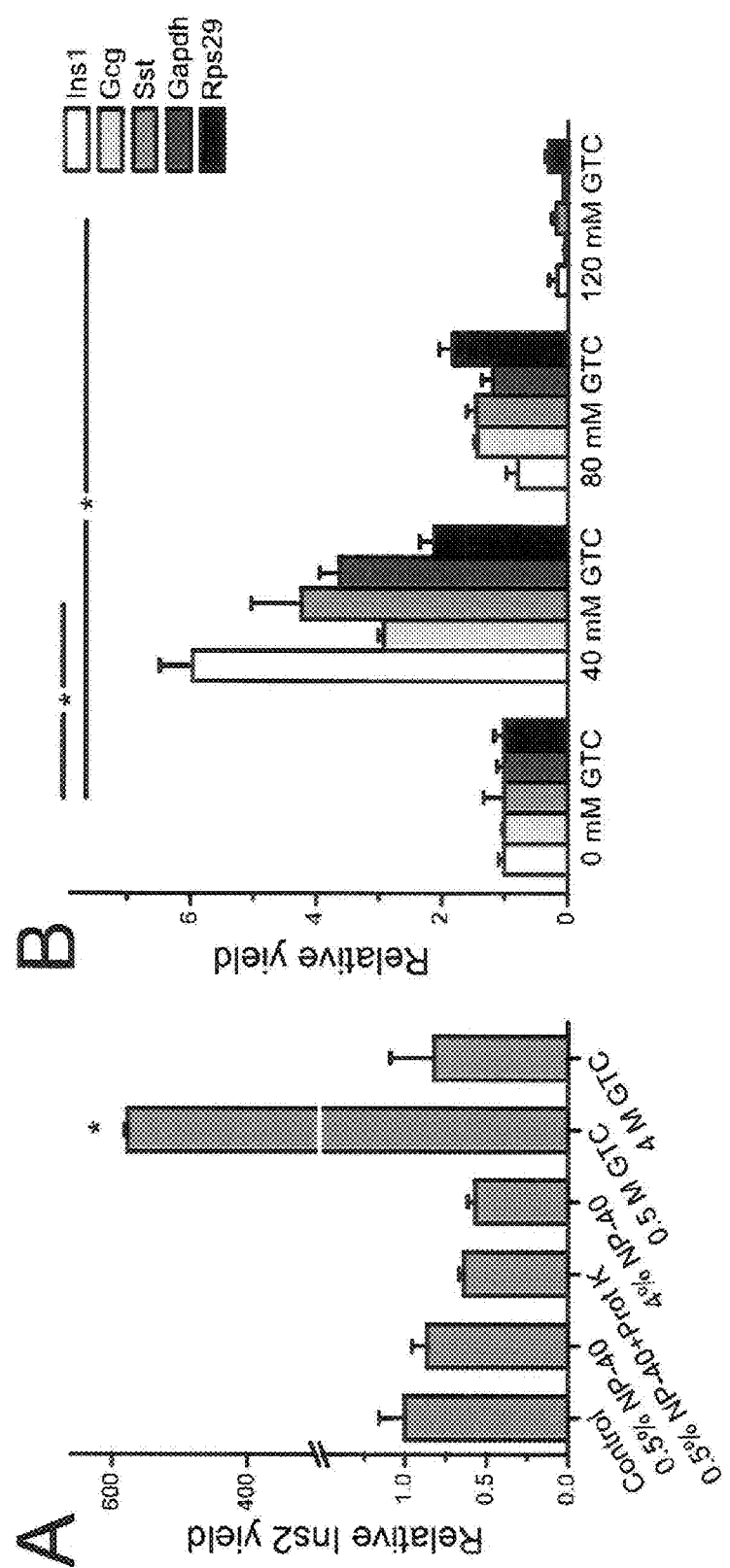
FIG. 2: Evaluation of lysis buffers. (A) Determination of lysis efficiency. Each bar indicates relative yield of Ins2 using a single pancreatic islet (2000 cells) as starting material. Each islet was treated with indicated concentrations of either NP-40, with and without proteinase K (Prot K), or guanidine thiocyanate (GTC). Only lysis with 0.5 M GTC had a significant effect compared to control conditions ($p<0.001$, n=3). (B) Effect of lysis buffers on RT reaction yield. Identical amounts of purified islet total RNA was used as starting material. Relative yields of five genes were analysed: Ins1, Gcg, Sst, Gapdh and Rps29. Increasing concentrations of guanidine thiocyanate was added to the RT reaction. There is a significant difference for all genes between control and 40 mM or 120 mM ($p<0.05$) but not 80 mM. Values are mean±SEM for 3 separate experiments.

The purpose of the lysis buffer is to make the mRNA accessible for the RT enzyme. Two detergents were chosen for this task, a weak, non-chaotropic (Igepal CA-630, a.k.a. NP-40) and a strong, chaotropic (guanidine thiocyanate, GTC). The lysis efficiency and potential influence on the downstream RI reaction was evaluated. Five different lysis conditions were evaluated in terms of their ability to lyse one pancreatic islet (FIG. 2A). NP-40 had no effect compared to control (water) when used at concentrations of 0.5% or 4%. Proteinase K had no effect when added in the presence of 0.5% NP-40. GTC based lysis buffer provided efficient lysis of the islet using a concentration of 0.5 M and increased the RNA yield 600-fold; an effect that was strongly diminished at 4 M.

Then, the lysis buffers with respect to their effect on the RT-reaction were compared. Low concentrations (0.1%) of NP-40, regardless of addition of proteinase K, did not have an effect compared to control conditions. However, when used at a concentration of 1%, NP-40 resulted in small but significant improvement of RT-efficiency. In FIG. 2B, three concentrations of GTC (40 mM, 80 mM, and 120 mM) were tested on five genes. The reaction efficiency was significantly improved (2-6 fold) for all tested genes using 40 mM GTC. By contrast, 80 mM GTC had no effect whereas 120 mM GTC was in fact inhibitory. The addition of 0.5-1-5% 2-mercapto ethanol did not improve the yield of the RT reaction either alone or in concert with GTC (data not shown). Formation of correct PCR-products was confirmed by agarose gel electrophoresis. Of the tested detergents, GTC was chosen due to superior lysis ability and positive effect on the RT reaction at the concentration of 40 mM.

Optimization of RT Priming

Figure 3A:
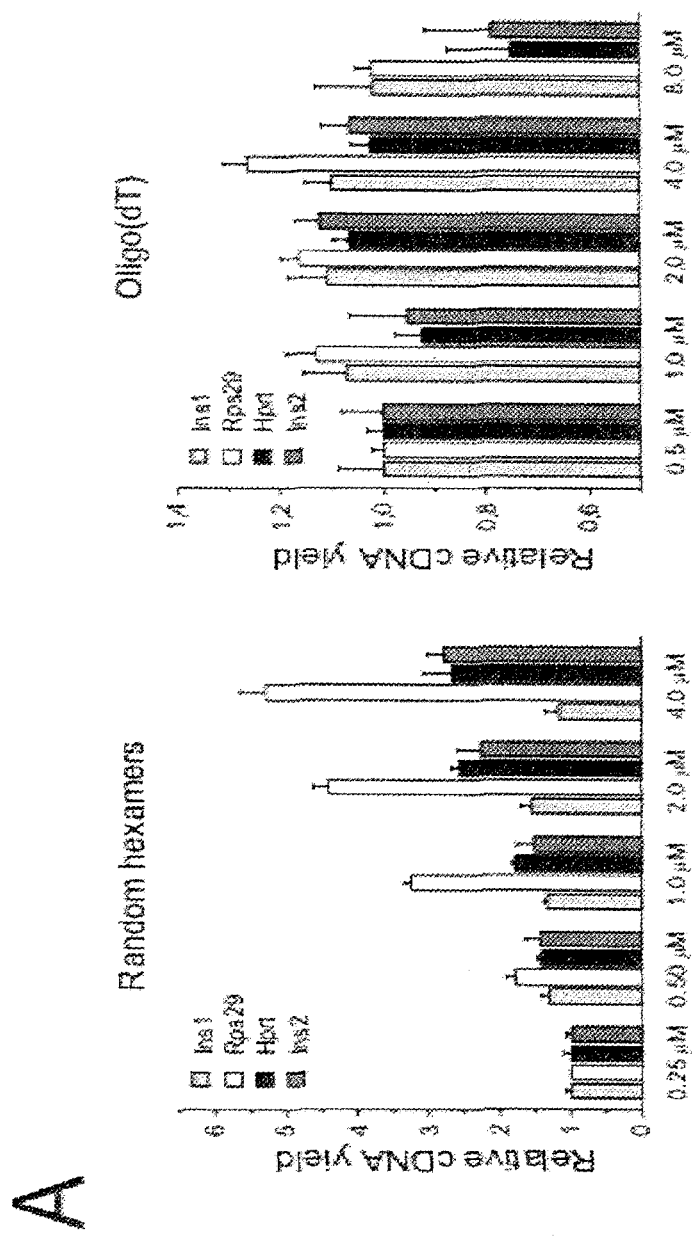
FIG. 3: Optimization of the RT reaction. Four genes were measured: Ins1, Ins2, Rps29 and Hprt. (A) Determination of optimal RT primer concentration using either oligo(dT) or random hexamers. (B) Comparison of RT priming strategies and temperature profiles. Identical amounts of purified total RNA from MIN6 cells was used as starting material. Relative RT reaction yields are shown for various primer combinations. 2.0 µM of either oligo(dT) or random hexamers or both was used. Temperature profiles used are isothermal (black bars), gradient (white bars) and cycled (grey bars). Values are mean±SEM for 3 separate experiments.
Figure 3B:
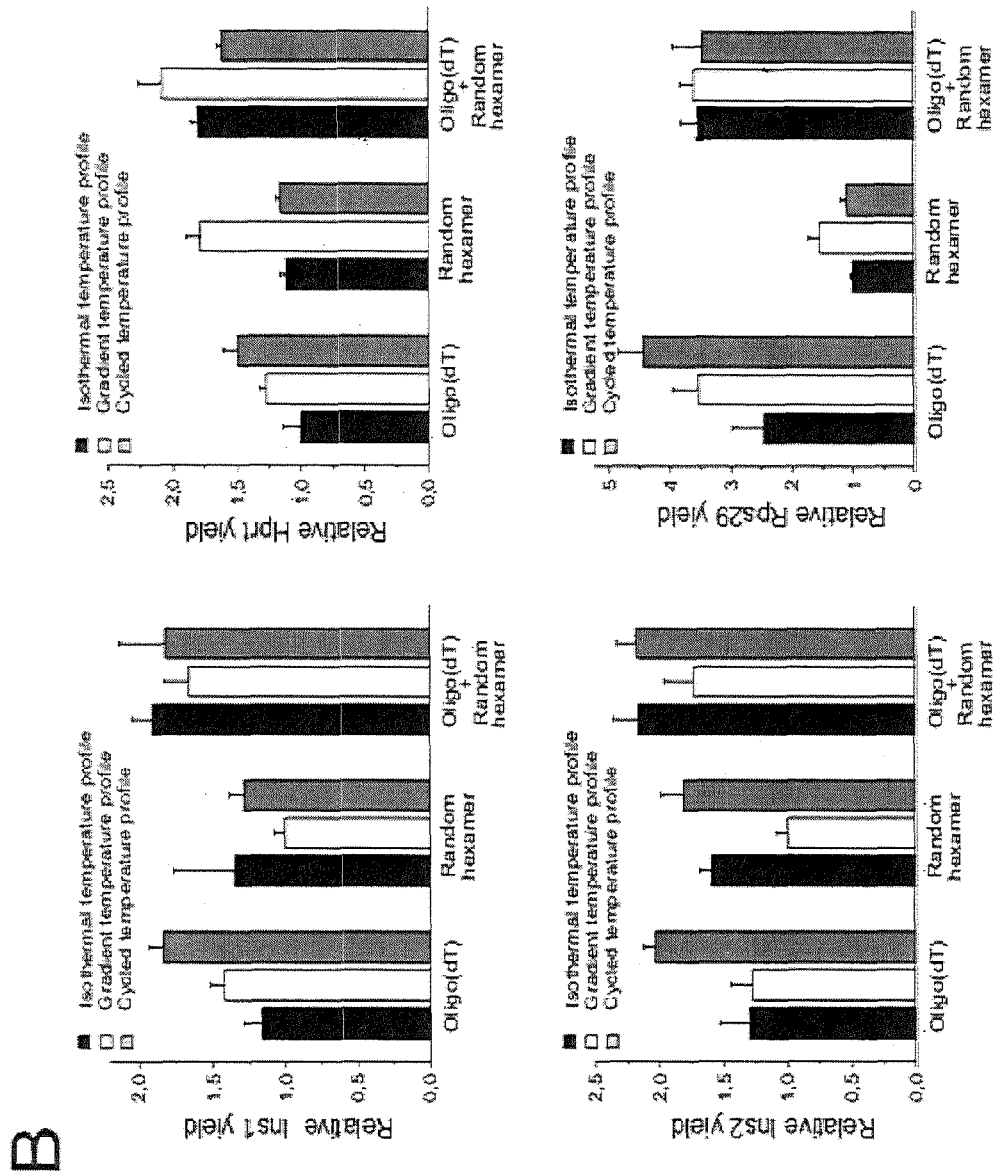

Proper quantification of rare transcripts requires efficient cDNA generation by reverse transcription (RT). In FIG. 3, priming of the RT reaction by random hexamers and oligo (dT) nucleotides were investigated for four genes: insulin 1 (Ins1), insulin 2 (Ins2), ribosomal protein S29 (Rps29) and hypoxanthine guanine phosphoribosyl transferase (Hprt). The effect of RT primer concentration was analyzed (FIG. 3A). The RT efficiency generally increased with increasing primer concentration, although there were some differences between the measured genes. 2.0 μM of either oligo(dT) or random hexamer priming result in a high cDNA yield. In FIG. 3B, the effect of combining RT-primers and temperature profiles was tested. Three different temperature profiles (isothermal, gradient and cycled temperature profiles) were evaluated in combination with random hexamer and oligo(dT) priming strategies. The combination of both priming methods were in all cases superior or equal to the single best priming method used. It could be hypothesized that the initiation of the RT reaction, at which stage the RT primer anneals to its target mRNA molecule, is critical. A gradually increasing temperature (gradient) would allow low melting point RT primers to anneal to its target, while strong secondary structures denature in the later stages of the incubation. A cycled temperature profile was also tested which was recently reported to increase the cDNA yield for quantification of miRNA [14]. However, there was no significant difference in yield or reproducibility between the tested temperature profiles. There was 2-5-fold difference between worst and best primer/temperature combination. One can conclude that a combination of 2.0 μM oligo(dT) and 2.0 μM random hexamers maximizes the yield of the RT reaction.

In addition to oligo(dT) and random hexamer priming, RT-priming with gene-specific primers (GSP) was tested. For some genes, concentration dependent formation of non-specific products in the downstream PCR was observed. This effect was pronounced when using a mixture of different GSPs. To determine whether this was an effect on the RT or the PCR, GSPs were added directly to the PCR. A total concentration >0.4 μM GSPs in the PCR resulted in formation of erroneous PCR products. However, dilution of cDNA reverse transcribed with GSP did only partly remove the formation of unspecific products. Thus, high concentrations of GSPs affect both RT and PCR reactions negatively.

Technical Reproducibility

Figure 4:
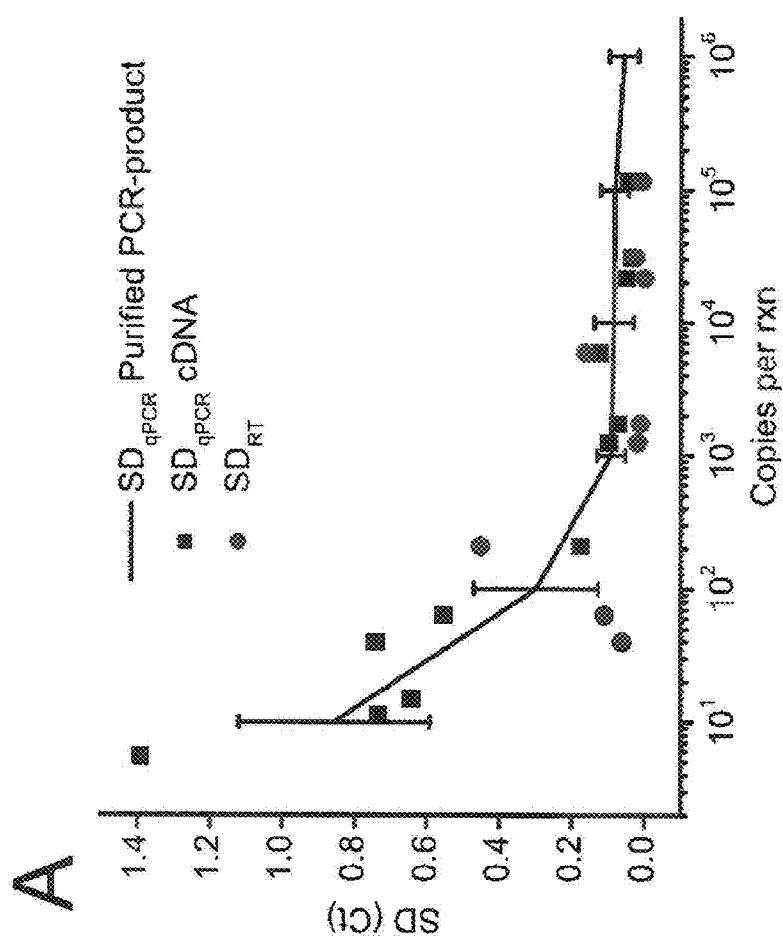
FIG. 4: Technical reproducibility of RT and qPCR. (A) Dilutions of purified total islet RNA, equivalent with the amount found in a single cell, were run in triplicate RT and triplicate qPCR reactions. Standard deviation (SD) of measurements on three genes (Ins1, Ins2 and Gcg) is shown, with the contribution from qPCR (black squares) and RT (red circles). The SD of qPCR triplicate reactions based on pre-determined amounts of purified PCR product of Ins1, Ins2, Gcg, Rps29 and Hprt are shown as reference (solid black line). The variability between these five assays is shown as (SD) error bars. (B) Single β-cells were measured with triplicate RT and duplicate qPCR reactions to visualize the variability in single cell mRNA measurements. The Ins2 copy number refers to numbers of molecules in the RT reaction. Approximately 3% of the original cell was analyzed in each reaction.

The technical reproducibility of RT and qPCR is presented in FIG. 4A. The reproducibility of the RT and qPCR reaction, represented here by standard deviation in Ct values (SDRT and SDqPCR respectively), are shown for a range of different initial copy numbers In addition, SDqPCR was calculated from dilution of purified PCR-product. There is no difference between SDqPCR from cDNA or PCR-product, indicating that the technical reproducibility is intrinsic of the qPCR reaction itself and not due to interfering factors from upstream reactions. All reactions are highly reproducible down to ~1000 copies (approx. Ct 28-30), and acceptable down to ~100 copies. At <100 copies the variability in the RT and PCR reactions is a considerable obstacle for accurate quantification of mRNA. FIG. 4B shows the technical variation in context of the biological, cell-to-cell variation. Single cells from the islets of Langerhans in mice were collected and analyzed in triplicate RT reactions and duplicate qPCR reactions. The technical variation is on par with the one observed in FIG. 4A. Though the cell-to-cell variation for the collected β-cells was relatively small, the technical variation is smaller, and allows absolute quantification with sufficient accuracy in the range of 100-200 molecules.

For analysis of gene expression profiling in single cells from the endocrine pancreas of the mouse, Ins1, Ins2, glucagon (Gcg), Rps29 and chromogranin B (Chgb) were measured in 158 cells collected from four incubations with different glucose concentrations (3, 6, 10 and 20 mM). Islets of Langerhans in the pancreas are heterogeneous and contains 1000-3000 cells comprising at least four endocrine cell types, where insulin-secreting β-cells and glucagon-producing α-cells are the most abundant [18]. Based on presence of insulin or glucagon transcripts, these cells were distinguished as β-cells (126 cells, 83%), α-cells (25 cells, 16%) or unknown (1 cell, 0.7%). Six samples were negative for all measured genes and they were categorized as technical failures (96% success rate). For all genes, lognormal distribution was confirmed and the geometric means were calculated as shown in the following table:

TABLE 1

Statistical parameters describing gene expression in single pancreatic α- and β-cells

| Gene | N[1] | Geometric mean | $\log_{10}$ Geometric mean (SD) | Shapiro Wilk P-value[2] |
|---|---|---|---|---|
| Ins2 | 124 | 8900 | 3.9 (0.5) | 0.53 |
| Ins1 | 100 | 3100 | 3.5 (0.5) | 0.57 |
| Gcg | 25 | 19000 | 4.3 (0.3) | 0.25 |
| Rps29 | 102 | 230 | 2.4 (0.3) | 0.98 |
| Chgb | 59 | 82 | 1.9 (0.5) | 0.67 |

[1]N is the number of cells expressing the tested gene. $N_{tot}$ = 158.
[2]A high Shapiro-Wilk value reflects a good fit, in this case to the lognormal distribution.

The data allowed for a correlation of expression levels in the individual cells as it is shown in the following table. The Pearson correlation factor for Ins1 and Ins2 was 0.59, which indicates single cell correlation.

TABLE 2

Pearson correlation coefficients of expression levels in single cells

| | Ins2 | Ins1 | Gcg | Rps29 | Chgb |
|---|---|---|---|---|---|
| Ins2 | 1 | | | | |
| Ins1 | 0.59 | 1 | | | |
| Gcg | N.A. | N.A. | 1 | | |
| Rps29 | 0.18 | 0.19 | −0.25 | 1 | |
| Chgb | 0.08 | 0.14 | 0.06 | 0.31 | 1 |

Figure 5:
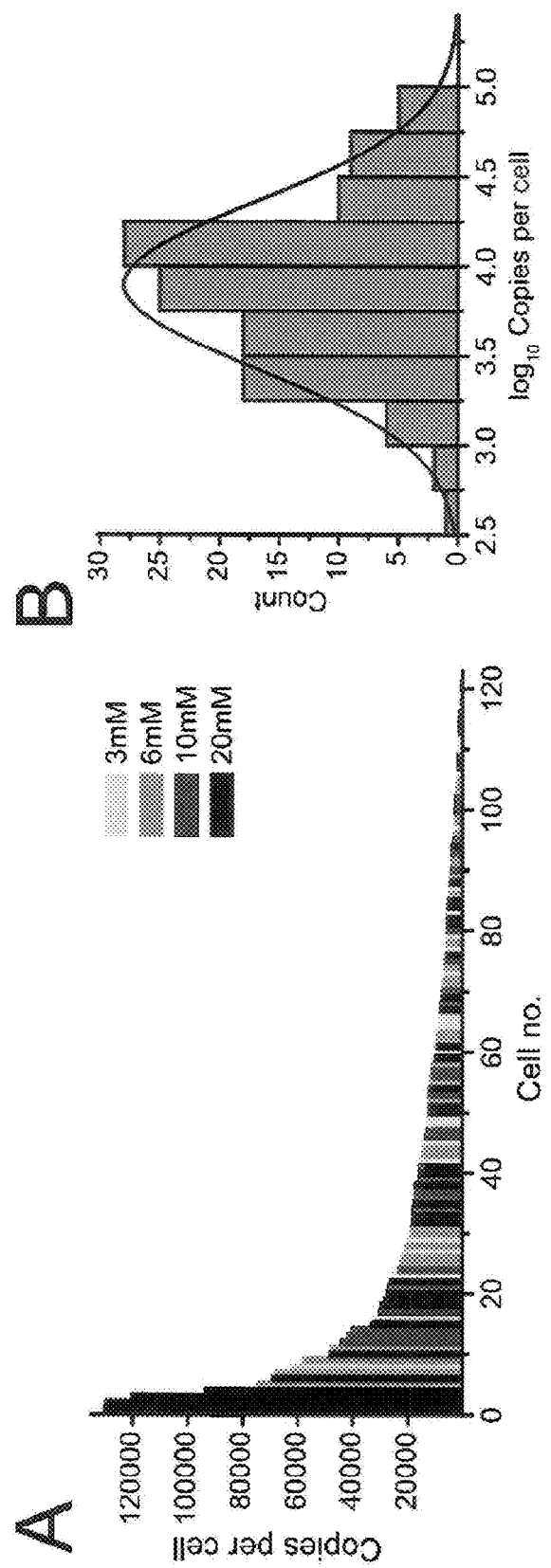
FIG. 5: Ins2 transcripts quantified in 126 β-cells from the Islets of Langerhans. (A) The expression level of Ins2 for each β-cell, incubated in 3, 6, 10 or 20 mM glucose, as indicated. (B) The histogram shows that the expression levels of Ins2 are log normally distributed. Transcript levels are mean-centered for the four glucose concentrations.
Figure 6:
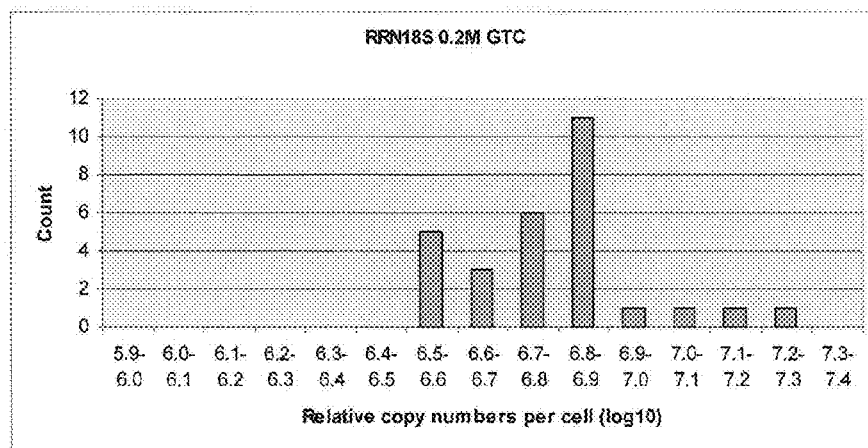
FIG. 6: Genes' expressions in individual cells collected by Fluorescence Activated Cell Sorting (FACS), extracted using the disclosed invention, and measured with reverse transcription and qPCR. Beta actin cDNA measured in individual cells from which mRNA was extracted in 0.2 M GTC (top), 0.1 M GTC (middle) and in pure water (bottom).
Figure 6:
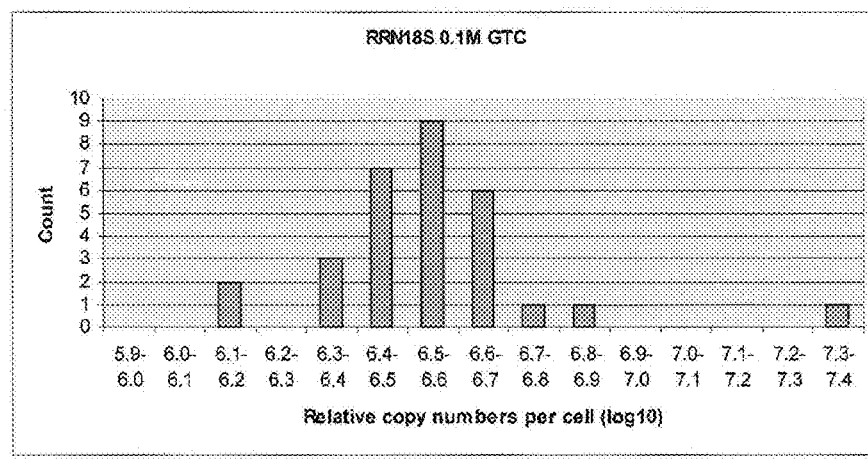
Figure 6:
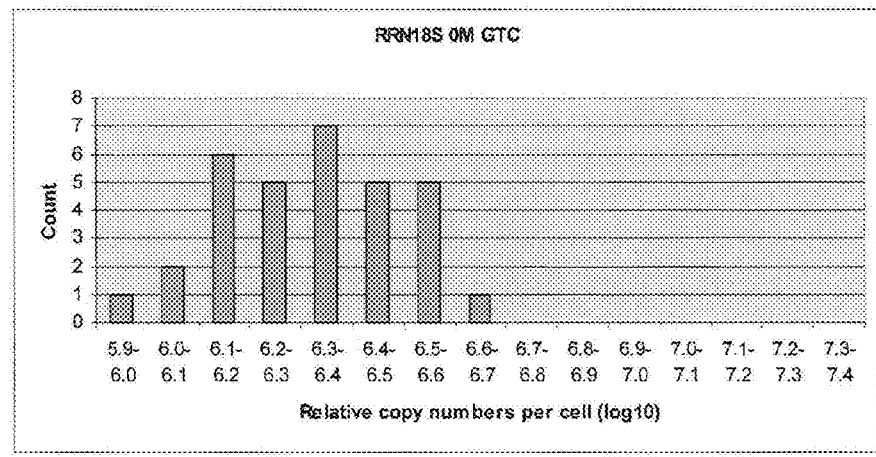
Figure 7:
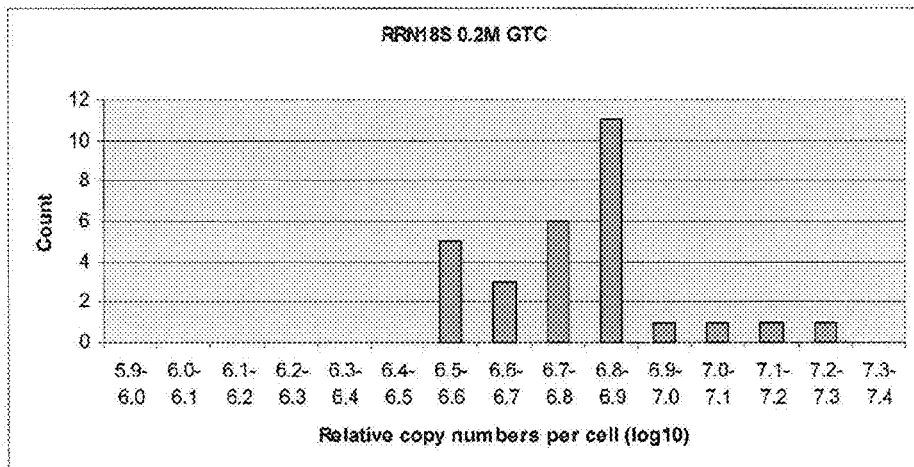
FIG. 7: RRN18S cDNA measured in individual cells from which mRNA was extracted in 0.2 M GTC (top), 0.1 M GTC (middle) and in pure water (bottom). X-axis shows the relative amount of cDNA present per cell in logarithmic scale.
Figure 7:
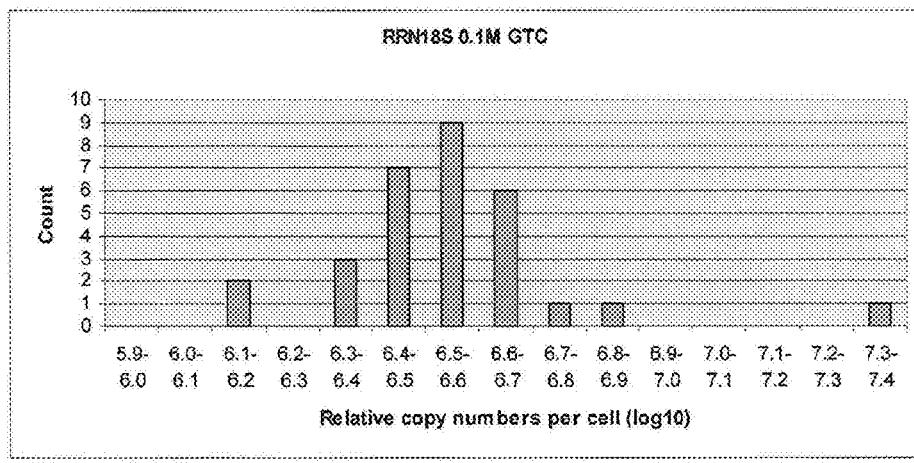
Figure 7:
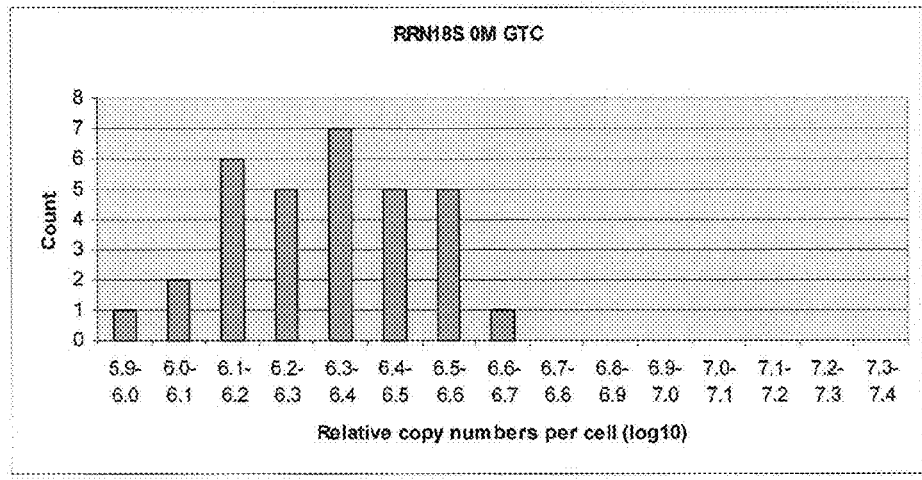
Figure 8:
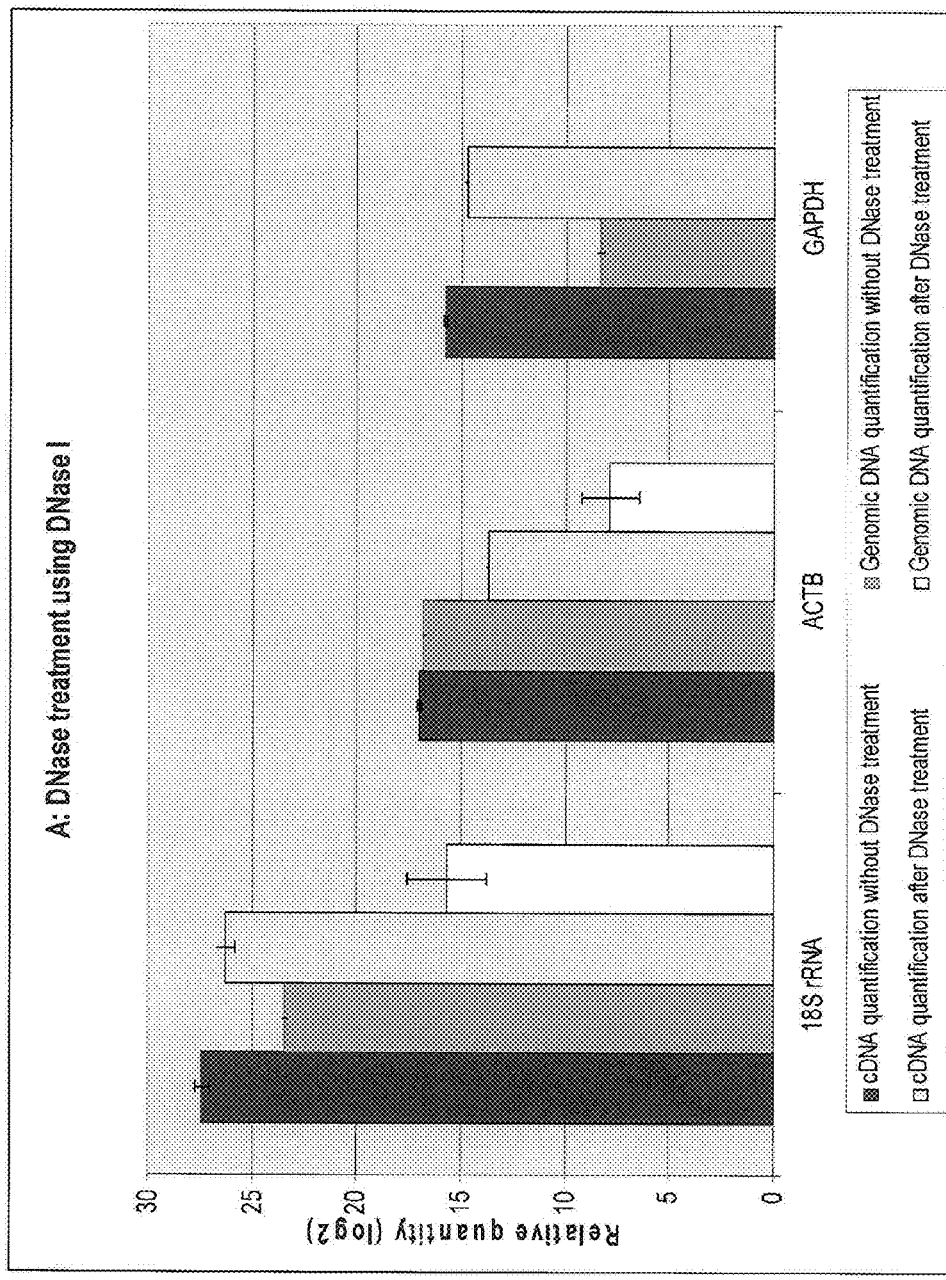
FIG. 8: Mean and standard deviation of the relative amount of 18S, ACTB and GAPDH DNA determined by QPCR after treatment with the disclosed invention. The studied RNA samples were spiked with genomic DNA and treated with either DNase I (FIG. 8A) or shrimp nuclease (FIG. 8B). Controls without nuclease treatment are presented, as well as sample not treated with reverse transcriptase (No RT controls), which only contain genomic DNA.
Figure 8A:
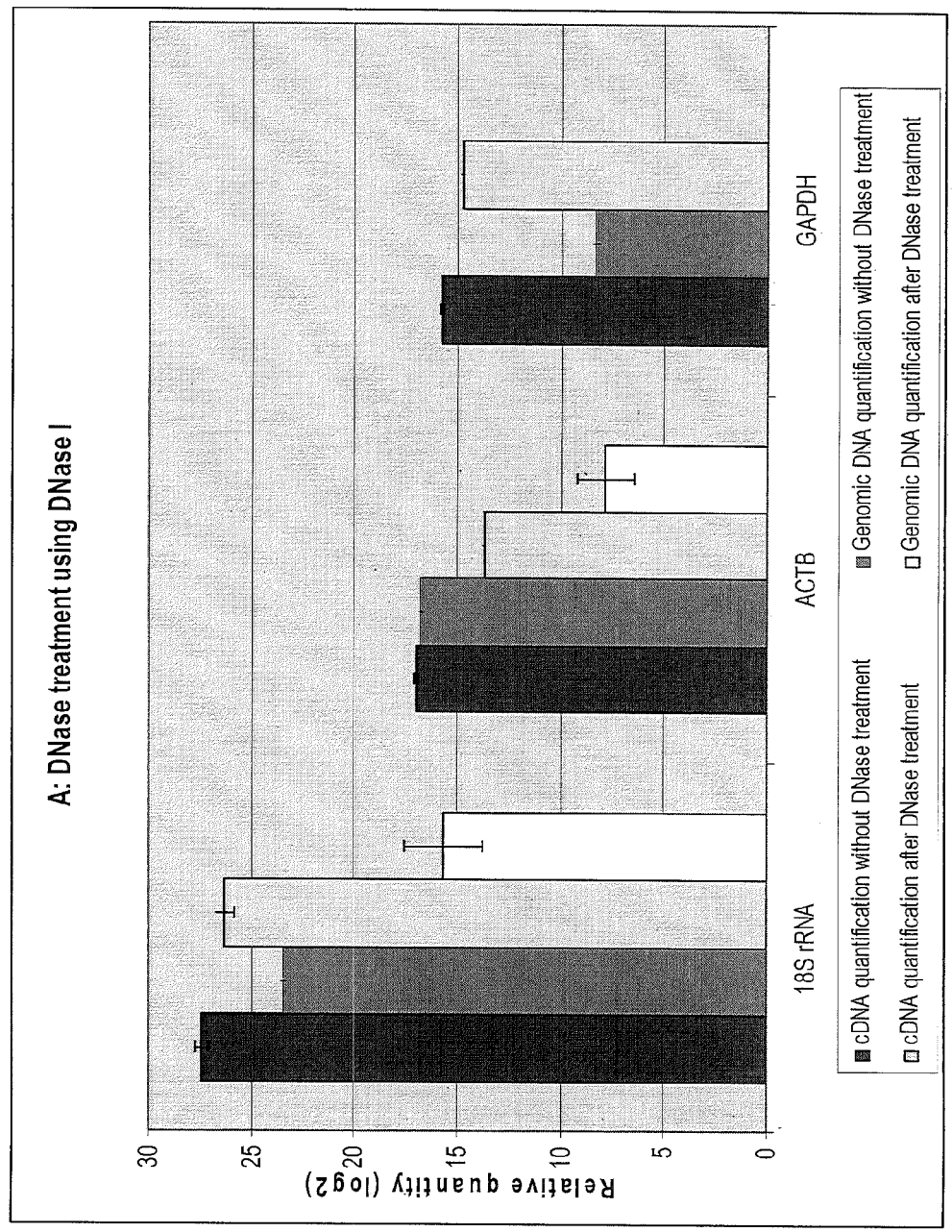
Figure 8B:
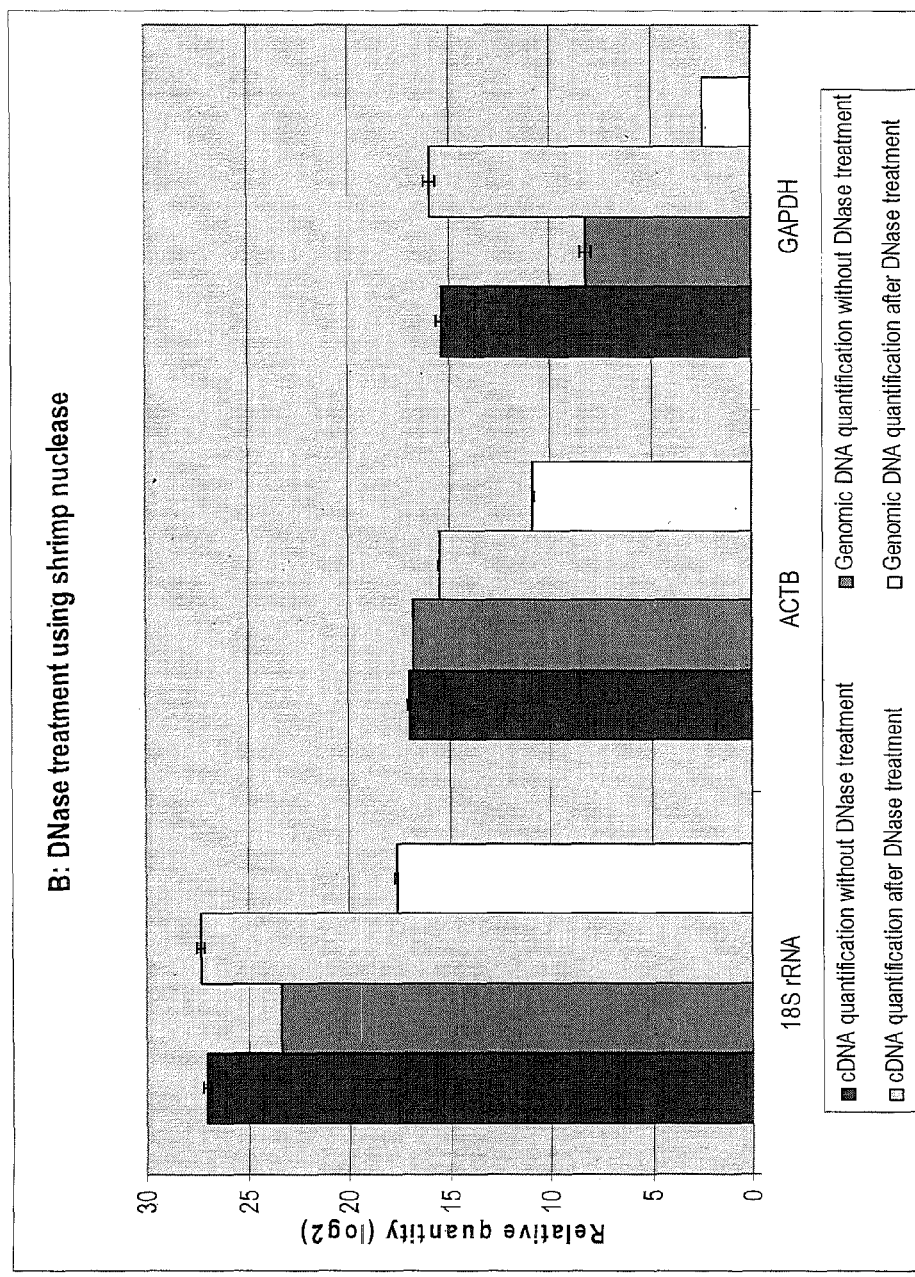

All populations of cells showed a large heterogeneity in transcript levels. For example, of the 35 (3-cells incubated in 20 mM glucose, the four cells with highest expression account for 50% of the total Ins2 mRNA (FIG. 5A). As indicated in studies on pooled cells, increasing glucose concentration had a stimulating effect on Ins1, Ins2 and Chgb and a slight negative effect on Gcg. A stronger effect of glucose on insulin and glucagon in the cells with high expression levels was observed. Out of the 14 cells with the highest Ins2 levels (top 20%), 11 were incubated in 20 mM glucose while three were in 3 mM glucose. Corresponding ratio between 20 and 3 mM glucose incubations were 12 to 1 for Ins1 and 0 to 2 for Gcg. Expression levels were normally distributed for all genes at every glucose concentration.

Like any investigation of small and sensitive mechanisms, single cell transcription profiling requires careful preparations and highly optimized reaction conditions for a successful outcome. The results of the disclosed study allows definition of optimal conditions that will enable to experimenter to avoid pitfalls by using the right reagents at the ideal concentrations.

While the effect on lysis is indisputable and expected—i.e. GTC was superior in lysing the islet—its effect on the RT reactions is more complex. While high concentrations (>100 mM) severely disturb the reaction, low concentrations (~40 mM) has a favorable effect on the RT yield. GTC is a strong chaotropic detergent. The positive effect of GTC may act by reducing secondary structures, thus allowing greater access to the mRNA for primers and reverse transcriptase.

According to the present invention, it is preferred to use a combination of random hexamer and oligo(dT) in the RT reaction irrespective of the temperature profile used. In agreement with previous findings [16], the results are highly gene dependent and thorough optimizations is needed for highest possible RT efficiency. Priming of RT by gene-specific primers (GSP) is occasionally used in mRNA quantification. There are two explanations to the formation of unspecific PCR products of cDNA primed with GSPs: Firstly, the total primer concentration in the cDNA used in the PCR can reach levels approaching that of the PCR primers. This could interfere with the amplification and generate unspecific products. Secondly, GSPs bind largely unspecific to the mRNA [16]. Thus, the resulting cDNA will be similar to that of random hexamer priming, but with the GSP primer in the 3' end.

In five measurements of a cell with 100 copies of a particular transcript, the results will span approximately 10-40 copies per reaction (corresponding to 50-200 copies per cell). This spread is mostly due to variation in the qPCR, and it is in line with the biological variation between cells. Duplicate or triplicate qPCR reactions will provide increased accuracy, and allow quantification of lower levels.

In addition, the reproducibility of results obtained with single cell preparations in NP40 in milliQ water was compared with preparations in 0.3 M GTC by means of calculating the standard deviations of 6 RT-PCR reactions each. For this experiment, each cell was divided into three RT replicates and each of these were later divided into PCR duplicates. Hence, the standard deviation (SD) was based on six samples. The results showed that the standard deviation was is substantially lower (and therefore reproducibility higher) for cells prepared in 0.3 M GTC.

Summarizing, according to the method of the present invention, the cells are deposited in the strong detergent guanidine thiocyanate, optionally together with an RNA spike for quality assessment. 30 to 50 mM concentration of guanidine thiocyanate is a potent reverse transcription reaction enhancer. A combination of random hexamer and oligo (dT) priming ensures a high cDNA yield.

EXAMPLES

Example 1

Preparation and Culture of Cells

Pancreatic islets were prepared from healthy female National Maritime Research Institute (NMRI) mice aged 3-4 months (Bomholtgaard, Ry, Denmark) and fed a normal diet ad libitum. The mice were sacrificed by cervical dislocation, and pancreatic islets were isolated by collagenase P digestion (Roche, Basel, Switzerland) followed by manual collection of islets. All experimental procedures involving animals were approved by the ethical committee of Lund University. To prepare dispersed single cells the collected islets were gently shaken at low extracellular $Ca^{2+}$ concentration to dissolve the structure of the islet [21]. Dispersed cells were plated on plastic 35 mm Petri dishes (Nuns, Roskilde, Denmark) in RPMI 1640 medium (SVA, Uppsala, Sweden) supplemented with 10% FCS, 100 U $mL^{-1}$ penicillin, and 10 $\mu gmL^{-1}$ streptomycin (all from Invitrogen, Carlsbad, Calif., USA) in the presence of various concentrations of glucose (Sigma-Aldrich, St. Louis, Mo., USA). The cells were maintained in culture 18-24 hours for the glucose stimulation experiment and for 2-6 hours for other experiments.

MIN6 cells were cultured in 5 mM glucose as previously described [2].

Example 2

Single Cell Collection

Attached dispersed cells were washed twice with a buffer containing 138 mM NaCl, 5.6 mM KCl, 1.2 mM $MgCl_2$, 2.6 mM $CaCl_2$, 5 mM HEPES (pH 7.4 with NaOH) and 3-20 mM glucose (same glucose concentration as in culture) to remove dead and loose debris for cell collection with patch-clamp pipettes. The dish, containing adhered cells and approximately 1 mL buffer, was mounted in a standard inverted light-microscope (Zeiss Axiovert 135, Oberkochen, Germany). Borosilicate glass capillaries (Hilgenberg GmbH, Malsfeld, Germany) with outer diameter of 1.6 mm and wall thickness of 0.16 mm were pulled to pipettes using a patch-clamp pipette puller (Heka PIP5, Lambrecht, Germany). The diameter of the tip was approximately 10 μm on average, substantially wider than standard patch-clamp pipettes and large enough to allow passage of an intact cell. The glass pipette was mounted on a hydraulic micromanipulator (Narishige, Tokyo, Japan) on the microscope. By controlling the pressure inside the pipette it was possible to collect intact or nearly intact cells with minimum volume of extracellular solution.

Example 3

Lysis and Purification

Islet lysis: Single pancreatic islets of roughly the same size and about 1000 cells were placed in 10 μl of various lysis buffers. The detergents Nonidet P-40 (NP-40, a.k.a. Igepal CA-630, Sigma-Aldrich) and guanidine thiocyanate (GTC, Sigma-Aldrich) were used. Samples were incubated at 60° C. or 80° C. for 15 minutes (60° C. for samples containing 0.4 mg/ml proteinase K (Invitrogen)) followed by 5 min incubation at 95° C. and frozen at −25° C. for subsequent analysis. Samples were diluted 1:20 prior reverse transcription to minimize possible inhibitory effects.

Single Cell Lysis:

In single cell experiments, the glass pipettes were emptied in 0.2 ml plastic tubes containing 2 μl of lysis solution. The emptying required a custom-made device, consisting of a tube holder lined up with a coarse micromanipulator on which the pipette was mounted. The glass pipette was carefully flushed with lysis buffer a few times to make sure the cell entered the tube. In most cases, the tip of the pipette was gently broken in the tube thereby facilitating the flushing of the pipette. Tubes were then immediately placed on a heating block with heated lid at 80° C. for 5 minutes. Several compositions of the lysis buffers, containing either NP-40 or GTC, were evaluated. Unless indicated otherwise, the detergents were diluted in mQ purified water, but occasionally in a buffer containing 50 mM Tris-Cl pH 8.0, 140 mM NaCl, 1.5 mM $MgCl_2$ (all Sigma) was used. Following the heat treatment, the samples were immediately frozen on dry ice (−78° C.) and stored at −80° C. for subsequent reverse transcription.

Total RNA Extraction:

Some optimization experiments were performed with total RNA from larger cell populations. Total RNA was purified with GenElute Mammalian Total RNA Kit (Sigma-Aldrich) and concentrations were measured with a NanoDrop ND-1000 spectrophotometer (Nanodrop Technologies, Wilmington, Del., USA).

Example 4

In Vitro Transcription

To generate an artificial RNA control we used the T7 RNA Polymerase in vitro transcription system (Takara, Shiga, Japan). A PCR assay for cyclophilin E (Ppie) was used as template for the in vitro transcription. First, the Ppie PCR product was generated using the same setup as for the real-time PCR assays, except that all fluorophores were excluded. The PCR product was purified using PCR purification kit (Qiagen, Hilden, Germany) and then amplified again in a new PCR reaction with an extended forward PCR primer where the promoter sequence for T7 RNA Polymerase was added. The final PCR product was purified as above and used in the in vitro transcription reaction, according to the manufacturer's instruction. The 20 μL reaction mix contained: 40 mM Tris-HCl (pH 8.0), 8 mM $MgCl_2$, 2 mM spermidine, 5 mM dithiothreitol (all Takara), 2 mM NTP (Invitrogen), 20 U RNaseOut (Invitrogen) and ~40 ng template DNA. The reaction was incubated at 42° C. for 1 h.

Example 5

Reverse Transcription

The reverse transcriptase SuperScript III (Invitrogen) was used throughout the study [17]. 6.5 μL containing total RNA or lysed single cells, 0.5 mM dNTP (Sigma-Aldrich), 2.5 μM oligo(dT) (Invitrogen), 2.5 μM random hexamers (Invitrogen) and if indicated 0.5 μM of each gene specific primer (identical to reverse PCR primer, Invitrogen or MWG-Biotech, Ebersberg, Germany) were incubated at 65° C. for 5 min. Various combinations of RT-primers were used in this work and alternative strategies are described in the results. We then added 50 mM Tris-HCl (pH 8.3), 75 mM KCl, 3 mM $MgCl_2$, 5 mM dithiothreitol, 20 U RNaseOut and 100 U SuperScript III (all Invitrogen) to final volume of 10 μL. Final reaction concentrations are shown. The temperature profiles used were: isothermal, 25° C. for 5 min, 50° C. for 45 min; gradient, 25-40° C. for 1 min/° C., 41-65° C. for 5 min/° C.; cycled, 50 cycles at 25° C. for 30 sec, 50° C. for 30 sec and 55° C. for 5 sec. All reactions were terminated at 70° C. for 15 min. For calculations of standard deviation of the RT-qPCR reaction, triplicate RT and triplicate qPCR reactions on diluted purified total mouse islet RNA was used [16].

Example 6

Quantitative Real-Time PCR

Real-time PCR measurements were carried out on the ABI PRISM 7900HT Sequence Detection System (Applied Biosystems, Foster City, Calif., USA) in 10 och 20 µL reactions. The PCR mix contained: 10 mM Tris (pH 8.3), 50 mM KCl3 mM MgCl2, 0.3 mM dNTP, 1 U JumpStart Taq polymerase (all Sigma-Aldrich), 0.5×SYBR Green I (Invitrogen), 1× Reference Dye (Sigma-Aldrich) and 400 nM of each primer (MWG-Biotech). Formation of expected PCR products was confirmed by agarose gel electrophoresis (2%) for all assays, and melting curve analysis for all samples. Real-time PCR data analysis was performed as described, and PCR efficiencies were calculated from dilution series of purified PCR-products (QIAquick PCR purification kit, Qiagen) [12,19]. Absolute copy numbers of purified PCR products were calculated using the following molar absorptivity values (in Moles-1 cm-1): dAMP, 15200; dTMP, 8400; dGMP, 12010; dCMP, 7050. A260 was measured with the NanoDrop ND-1000 spectrophotometer.

Example 7

Analysis of Individual Cells Sorted by Fluorescence Activated Cell Sorting

Individual THP1 monocytes were sorted into 96-well plates using Fluorescence activated cell sorting (FACS). Each well contained 100 ng polyinosinic acid, 500000 copies of an artificial RNA spike and either 2 µl 0.2M GTC, 4 µl 0.1M GTC or 10 µl $H_2O$. Reverse transcription (RT) was performed directly on the lysates in a 20 µl reaction volume (20 mM final GTC concentration per RT reaction) using the Transcriptor First Strand cDNA synthesis kit (Roche) with a blend of oligo(dT) and random hexamers. Two mRNAs, RRN18S and ACTB, were quantified per cell with qPCR and SYBR Green I Chemistry in a LightCycler480 (Roche).

Example 8

Removal of Deoxyribonucleic Acid as Integrated Step in the Disclosed Invention RNA samples contaminated with DNA were generated by spiking 5 ng of human total RNA (Roche) with 250 ng human genomic DNA. 2 ul of lysis buffer (0.2M GTC, 10 ng/ul poly(I)) was added to eight samples together with either $H_2O$ (4 samples) or 1 U nuclease (either DNase I or shrimp nuclease) with reaction buffer (4 samples) to a total volume of 6 ul. Samples were incubated at room temperature for 5 minutes and then the nuclease was inactivated by heating to 85° C. for 5 minutes in the presence of EDTA. Reverse transcription components were added to the samples using the Transcriptor First Strand cDNA Synthesis kit (Roche) with a blend of oligo(dT) and random hexamers in total volume of 20 µl (20 mM final GTC concentration per RT reaction). To further test the effect of nuclease treatment samples were extracted and QPCR amplified, but without reverse transcription (NoRT controls). Hence, no RNA is converted to cDNA and the QPCR measure the presence of the contaminating genomic DNA. All samples were assayed by QPCR for 18S rRNA, ACTB and GAPDH using SYBR Green I chemistry in a LightCycler480 (Roche).

Example 9

Improved Reproducibility with the Disclosed Invention

Figure 9:
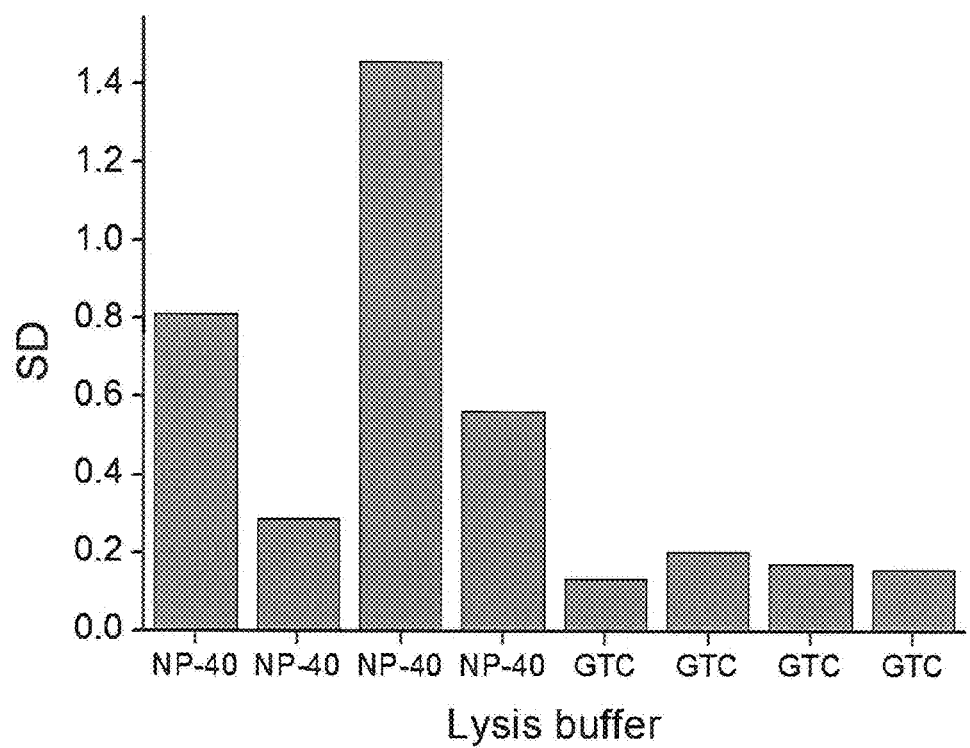
FIG. 9: Eight single-cell samples analyzed in triplicate RT-reactions for insulin II expression. Four of the single cell samples were extracted with lysis buffer containing 0.5%

Eight individual pancreatic β-cells were collected in either 0.5% NP-40 or in 0.5 M GTC according to the disclosed invention. After lysis the RNA was split in three reverse transcription reactions (SuperScript III, Invitrogen), cDNA was quantified by QPCR in a 7900 Taqman instrument from Applied Biosystems. The intra-assay variation, represented here by the standard deviation (SD) of the three CT values obtained for each of the eight cells, is shown in FIG. 9. The SD based on the disclosed invention was consistently lower demonstrating improved reproducibility of the disclosed process.

Example 10

Comparison Between Current State of the Art Technology and the Disclosed Invention Human cervical samples containing the human papilloma virus (HPV) was split into two aliquots of 300 µl each. The first aliquot was extracted using the state of the art RNeasy Micro kit (QIAGEN) according to the manufacturer's protocol. The second aliquot was extracted using the disclosed invention as follows. The aliquoted material was centrifuged for 5 minutes at 2300 g, washed with 500 µl PBS, centrifuged again for 3 minutes at 2300 g and the supernatant was discarded. 2 µl of GTC containing lysis buffer (0.2M) according to the disclosed invention was added. The aliquots were vortexed for one minute, transferred to 0.2 ml tubes and incubated at 80° C. for 5 minutes. Thereafter they were placed on ice.

Reverse transcription reagents were added in the form of the Transcriptor First Strand cDNA Synthesis kit (Roche) with a blend of oligo(dT) and random hexamers in a total volume of 20 µl (final GTC concentration was 0.2M). The presence of HPV16 was quantified with qPCR and FAM labelled TaqMan probes using the Eppendorf Realplex system. For HPV16E7 the difference in CT values with the two methods was 37.2–29.2=8, corresponding to about $2^8$=256 times more material being detected with the disclosed invention. HPV16E6 was only detected when the sample was extracted with the disclosed invention.

Example 11

Removal of Deoxyribonucleic Acid in Cervical Scrapes Samples as Integrated Step in the Disclosed Invention Caski cells with a total volume of 500 µl were extracted using the disclosed invention and reverse transcribed using the Transcriptor First Strand cDNA Synthesis kit (Roche) with a blend of oligo(dT) and random hexamers. The sample was incubated at 80° C. for 5 minutes. A DNase specific for double stranded DNA was added to the reverse transcription mix (a final concentration of 6 U shrimp DNase). Both the reverse transcription enzyme and the shrimp DNase were inactivated by heating to 85° C. for 5 minutes. The sample was analyzed by QPCR using an Eppendorf Realplex. Controls were run with reverse transcription and/or without DNase treatment. Treatment with DNase shifted CT values substantially to higher values evidencing that the DNase step to remove contaminating genomic DNA was successfully integrated in the disclosed invention.

Example 12

Analysis of Pelleted Monocytes with the Disclosed Invention Using Different Lysis Temperatures THP1 monocyte aliquots of approximately 35000 cells were pelleted by centrifugation at 300 g for 5 min and washed with 200 µl cold PBS. After removal of PBS, 2 µl of lysis buffer containing 0.2M GTC and 20 ng polyinosinic acid according to the present invention was added to each well. The samples were incubated at either 80° C. for 5 minutes or at room temperature for 10 or 20 minutes. Reverse transcription (RT) was performed directly on the lysates in a 20 µl reaction volume (final GTC concentration was 20 mM) using the Transcriptor First Strand cDNA synthesis kit (Roche) with a blend of oligo(dT) and random hexamers. Two mRNAs, RRN18S and ACTB, were quantified in each aliquot with qPCR and SYBR Green 1 detection in a LightCycler480 (Roche).

LIST OF ABBREVIATIONS USED

Ct, Cycle of threshold
GSP, gene specific RT-primer
qRT-PCR, quantitative reverse transcription polymerase chain reaction
RT, reverse transcription
SD, standard deviation

What is claimed is:

1. A method for performing a real time polymerase chain reaction (RT-PCR) for amplifying a target RNA comprising the steps of:
    lysing a biological sample which is supposed to contain the target RNA in a sample vessel with a lysis buffer comprising between 0.05 M and 1 M of Guanidine Thiocyanate and in the presence of NP40 (octyl phenoxylpolyethoxylethanol);
    diluting the sample to an extent such that the Guanidine Thiocyanate is present during a subsequent reverse transcription step in a concentration of 30 to 50 mM and such that the NP40 (octyl phenoxylpolyethoxylethanol) is present during the subsequent reverse transcription step at a V/V of 0.5 to 2% in the sample vessel;
    without any intermediate purification step, reverse transcribing the target RNA in a mixture of first strand cDNA synthesis primers into a first strand cDNA, the mixture consisting of primers hybridizing to a poly-A sequence or random primers or target specific primers in the sample vessel; and
    amplifying the first strand cDNA by means of subjecting the sample to multiple cycles of a thermocycling protocol.

2. The method according to claim 1, wherein the amplifying step is monitored in real time.

3. The method according to claim 1, wherein the biological sample consists of not more than 1000 cells.

4. The method according to claim 1, wherein the biological sample consists of not more than 100 cells.

5. The method according to claim 1, wherein the biological sample consists of not more than a single cell.

6. The method according to claim 1, wherein the lysis buffer comprises between about 0.2 and 0.5 M of Guanidine Thiocyanate.

7. The method according to claim 1, wherein the lysis step comprises the addition of a carbohydrate.

8. The method according to claim 1, wherein the lysis step is performed for at least 5 minutes at ambient temperature or below ambient temperature.

9. The method according to claim 1, wherein the lysis step is performed for at least 5 minutes at a temperature between about 55° C. to 85° C.

10. The method according to claim 9, wherein between the lysis step and the dilution step or between the dilution step and the reverse transcription step, the sample is incubated for at least 5 minutes at a temperature between about 80° C. to 90° C.

11. The method according to claim 8, wherein the lysis step is performed in the presence of DNAse I or Shrimp Nuclease.

12. The method according to claim 11, wherein between the lysis step and the dilution step or between the dilution step and the reverse transcription step, the sample is incubated for at least 5 minutes at a temperature between about 80° C. to 90° C.

13. The method according to claim 8, wherein prior to the dilution step, the sample is frozen at temperatures between about −20° C. and −80° C.

14. The method according to claim 1, wherein the mixture of cDNA synthesis comprises primers hybridizing to a poly-A sequence and random primers.

15. The method according to claim 14, wherein primers hybridizing to a poly-A sequence and random primers are present in essentially equal molar amounts.

16. The method according to claim 14, wherein the primers hybridizing to a poly-A sequence and random primers are present in concentrations between 1 µM and 5 µM each.

17. The method according to claim 14, wherein the primers hybridizing to a poly-A sequence and random primers are present in concentrations of about 2.5 µM each.

18. The method according to claim 7, wherein the carbohydrate is one of a sugar or a dextran.

19. The method according to claim 9, wherein the lysis step is performed in the presence of proteinase K.

* * * * *